United States Patent
Peeters et al.

(10) Patent No.: US 11,490,827 B2
(45) Date of Patent: Nov. 8, 2022

(54) INDUCTIVE SENSING SYSTEM FOR SENSING ELECTROMAGNETIC SIGNALS FROM A BODY

(71) Applicant: KONINKLIJKE PHILIPS N.V., Eindhoven (NL)

(72) Inventors: Wouter Herman Peeters, Waalre (NL); Mark Peter Paul Kleijnen, Eindhoven (NL); Gerardus Johannes Nicolaas Doodeman, Veldhoven (NL); Rick Bezemer, Amsterdam (NL); Jacobus Josephus Leijssen, Waalre (NL); Ronny Hubertus Johannes Grosfeld, Valkenswaard (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 662 days.

(21) Appl. No.: 16/475,394

(22) PCT Filed: Jan. 2, 2018

(86) PCT No.: PCT/EP2018/050044
§ 371 (c)(1),
(2) Date: Jul. 2, 2019

(87) PCT Pub. No.: WO2018/127482
PCT Pub. Date: Jul. 12, 2018

(65) Prior Publication Data
US 2019/0336014 A1 Nov. 7, 2019

(30) Foreign Application Priority Data
Jan. 9, 2017 (EP) .................................... 17150641
May 4, 2017 (EP) .................................... 17169584

(51) Int. Cl.
*A61B 5/0265* (2006.01)
*A61B 5/00* (2006.01)
*A61B 7/00* (2006.01)

(52) U.S. Cl.
CPC .......... *A61B 5/0265* (2013.01); *A61B 5/7225* (2013.01); *A61B 7/003* (2013.01);
(Continued)

(58) Field of Classification Search
CPC .... A61B 2560/0462; A61B 2562/0223; A61B 2562/166; A61B 2562/182;
(Continued)

(56) References Cited

U.S. PATENT DOCUMENTS

| 4,714,887 A | 12/1987 | Meissner |
| 8,386,273 B2 | 2/2013 | Kaminaga |

(Continued)

FOREIGN PATENT DOCUMENTS

| WO | 2006111877 A1 | 10/2006 |
| WO | 2018202486 A1 | 11/2018 |

OTHER PUBLICATIONS

International Search Report and Written Opinion, International Application No. PCT/EP2018/050044, dated Apr. 18, 2018.
(Continued)

*Primary Examiner* — Mark D Remaly

(57) ABSTRACT

The invention provides a magnetic inductive sensing system for sensing electromagnetic signals emitted from a body in response to electromagnetic excitation signals applied to the body. The electromagnetic signals are generated and sensed by the same loop resonator which comprises a single-turn loop antenna and a tuning capacitor. The loop antenna of the resonator and a signal generation means for exciting the resonator to generate excitation signals are together configured so as to optimize the value of a ratio between the radial
(Continued)

frequency of the generated electromagnetic excitation signals and a reference frequency of the antenna, where the reference frequency is the frequency for which one wavelength of the generated excitation signals (waves) matches the circumferential length of the antenna. This ratio, which corresponds to a normalized radial frequency of the generated excitation signals, is maintained between a value of 0.025 and 0.50.

20 Claims, 6 Drawing Sheets

(52) U.S. Cl.
CPC . *A61B 2560/0462* (2013.01); *A61B 2562/166* (2013.01); *A61B 2562/182* (2013.01); *A61B 2562/222* (2013.01)

(58) Field of Classification Search
CPC ... A61B 2562/222; A61B 5/0265; A61B 5/05; A61B 5/7225; A61B 7/003
See application file for complete search history.

(56) References Cited

U.S. PATENT DOCUMENTS

| | | |
|---|---|---|
| 2014/0197832 A1 | 7/2014 | Driesel et al. |
| 2015/0374292 A1 | 12/2015 | Wyeth et al. |

OTHER PUBLICATIONS

Teichmann, D. et al., "Respiration Monitoring Based on Magnetic Induction Using a Single Coil", Germany, 2010.
Cheng, D.,"The Reflected Impedance of a Circular Coil in the Proximity of a Semi-Infinite Medium", IEEE Transactions on Instrumentation and Measurement, vol. 14, No. 3, 1965.
Orfanidis, S., "Electromagnetic Waves and Antennas", Rutgers University, 2016.
Kwok, M., & Pepper, M. (1991). Noninvasive detection of ventricular wall motion by electromagnetic coupling Part 1: Theory. Medical and Biological Engineering and Computing, 29(2), 136-140.
Tarjan, P. P., & McFee, R. (1968). Electrodeless measurements of the effective resistivity of the human torso and head by magnetic induction. IEEE Transactions on Bio-Medical Engineering, 15(Oct. 1968), 266-278. http://doi.org/10.1109/TBME.1968.4502577.
Hart, L. W., Ko, H. W., Meyer, J. H., Vasholz, D. P., & Joseph, R. I. (1988). A noninvasive electromagnetic conductivity sensor for biomedical applications. IEEE Transactions on Biomedical Engineering, 35(12), 1011-1022. http://doi.org/10.1109/10.8686.
Yu, Z. Z., Peyton, a. T., Beck, M. S., Conway, W. F., & Xu, L. a. (1993). Imaging system based on electromagnetic tomography (EMT). Electronics Letters, 29(Feb. 1985), 625. http://doi.org/10.1049/el:19930418.
Vedru, J., Trolla, J., Humal, L. H., Lugna, V., & Vesselova, S. (1999). Magnitude Distribution of Foucault Cardiogram on Human Thoracic Surface. Medical & Biological Engineering & Computing, 37(1), 251-252. Retrieved from http://www.physic.ut.ee/~vedru/PUB/Distr_99.pdf.
Giiflilhs, H., Stewart, W. R., & Cough, W. (1999). Magnetic induction tomography. A measuring system for biological tissues. Annals of the New York Academy of Sciences. http://doi.org/101111/j.1749-6632.1999.tb09481.x.
Netz, J., Fomer, E., & Haagemann, S. (1999). Contactless impedance measurement by magnetic induction—a possible method for investigation of brain impedance. Physiological Measurement, 14, 463-471. http://doi.org/10.1088/0967-3334/14/4/007.
Korjenevsky, a, Cherepenin, V., & Sapetsky, S. (2000). Magnetic induction tomography: experimental realization. Physiological Measurement, 21(1), 89-94. http://doi.org/10.1088/0967-3334/21/1/311.
Scharfetter, H., Lackner, H. K., & Rosell, J. (2001). Magnetic induction tomography: hardware for multi-frequency measurements in biological tissues. Physiological Measurement, 22, 131-146. http://doi.org/10.1088/0967-3334/22/1/317.
Watson, S., Williams, R. J., Griffiths, H., Gough, W., & Morris, a. (2003). Magnetic induction tomography: phase versus vector-voltmeter measurement techniques. Physiological Measurement, 24, 555-564. http://doi.org/10.1088/0967-3334/24/2/365.
Watson, S., Morris, a, Williams, R. J., Griffiths, H., & Gough, W. (2004). A primary field compensation scheme for planar array magnetic induction tomography. Physiological Measurement, 25, 271-279. http://doi.org/10.1088/0967-3334/25/1/031.
Watson, S., Igney, C. H., Dössel, O., Williams, R. J., & Griffiths, H. (2005). A comparison of sensors for minimizing the primary signal in planar-array magnetic induction tomography. Physiological Measurement, 26, S319-S331. http://doi.org/10.1088/0967-3334/26/2/029.
Richer, a., & Adler, a. (2005). Eddy Current Based Flexible Sensor for Contactless Measurement of Breathing. 2005 IEEE Instrumentation and Measurement Technology Conference Proceedings, 1(May), 17-19. http://doi.org/10.1109/IMTC.2005.1604112.
Igney, C. H. H., Watson, S., Williams, R. J. J., Griffiths, H., & Dössel, O. (2005). Design and performance of a planar-array MIT system with normal sensor alignment. Physiological Measurement, 26, S263-S278. http://doi.org/10.1088/0967-3334/26/2/025.
Vauhkonen, M., Hamsch, M., & Igney, C. H. (2008). A measurement system and image reconstruction in magnetic induction tomography. Physiological Measurement, 29, S445-S454. http://doi.org/10.1088/0967-3334/29/6/S37.
Chen, Y., Yan, M., Chen, D., Hamsch, M., Liu, H., Jin, H., . . . Wang, Y. (2010). Imaging hemorrhagic stroke with magnetic induction tomography: realistic simulation and evaluation. Physiological Measurement, 31, 809-827. http://doi.org/10.1088/0967-3334/31/6/006.
Teichmann D, Foussier J, Jia J, Leonhardt S, Walter M. (2013). Noncontact monitoring of cardiorespiratory activity by electromagnetic coupling. IEEE Transactions on Biomedical Engineering, 60(8):2142-52. https://doi.org/10.1109/TBME.2013.2248732.
Teichmann, D., Kuhn, A., Leonhardt, S., & Walter, M. (2014). The MAIN Shirt: a textile-integrated magnetic induction sensor array. Sensors (Basel, Switzerland), 14, 1039-1056. http://doi.org/10.3390/s140101039.
Lee, Y. J., Lee, K. H., Kang, S. J., Kim, K. N., Khang, S., Koo, H. R. an, . . . Lee, J. W. (2014). Measurement of high-resolution mechanical contraction of cardiac muscle by induced eddy current. Conference Proceedings□: . . . Annual International Conference of the IEEE Engineering in Medicine and Biology Society. IEEE Engineering in Medicine and Biology Society. Annual Conference, 2014(1), 6286-6289. http://doi.org/10.1109/EMBC.2014.6945066.
Teichmann, D., De Matteis, D., Bartelt, T., Walter, M., & Leonhardt, S. (2015). A bendable and wearable cardiorespiratory monitoring device fusing two noncontact sensor principles. IEEE Journal of Biomedical and Health Informatics, 19, 784-793. http://doi.org/10.1109/JBHI.2015.2417760.
Gi, S. O., Lee, Y. J., Koo, H. R., Lee, S. P., Lee, K. H., Kim, K. N., . . . Lee, J. W. (2015). The Effect of Electrode Designs Based on the Anatomical Heart Location for the Non-Contact Heart Activity Measurement. Journal of Medical Systems, 39(12). http://doi.org/10.1007/s10916-015-0339-7.
Si, S. O., Lee, Y. J., Koo, H. R., Khang, S., Kim, K. N., Kang, S. J., . . . Lee, J. W. (2015). Application of a textile-based inductive sensor for the vital sign monitoring. Journal of Electrical Engineering and Technology, 10(1), 364-371. http://doi.org/10.5370/JEET.2015.10.1.364.

INDUCTIVE SENSING SYSTEM FOR SENSING ELECTROMAGNETIC SIGNALS FROM A BODY

CROSS-REFERENCE TO PRIOR APPLICATIONS

This application is the U.S. National Phase application under 35 U.S.C. § 371 of International Application No. PCT/EP2018/050044, filed on 2 Jan. 2018, which claims the benefit of European Patent Application No. 17150641.3, filed on 9 Jan. 2017 and European Patent Application No. 17169584.4, filed 4 May 2017. These applications are hereby incorporated by reference herein.

FIELD OF THE INVENTION

This invention relates to an inductive sensing system for sensing electromagnetic signals from a body, and in particular a sensor for inductively coupling with a body for sensing electromagnetic signals.

BACKGROUND OF THE INVENTION

Inductive sensing can be used as a means of non-invasive investigation of properties of a body.

In one advantageous area of application, inductive sensing can be used as a means of non-invasively investigating physiological characteristics, in particular heart and lung dynamics. Inductive sensing is based on magnetic induction and has several advantages over conductive and capacitive sensing.

An advantage compared to conductive sensing, such as bio-impedance measurements, is that adhesive electrodes are not required; sensing may be performed without contact and/or through non-conductive material, such as textile and plastic.

An advantage compared with capacitive sensing is that inductive sensing is based on magnetic fields rather than electric fields and as a result is more sensitive to changes at greater penetration depth inside the body, as opposed to those just occurring at skin level. This is because magnetic fields penetrate deeper into a body than electrical fields, and thus magnetic fields can be used to measure changes in properties deeper inside the body, whereas electrical fields are predominantly useful only for measuring effects at the surface of the skin such as changes in skin properties (e.g. permittivity) or movement of the skin (skin proximity).

Coil-based inductive sensors function by inductively coupling with electromagnetic signals (i.e. electromagnetic waves or oscillations), wherein propagation of the signals through the coil leads to a change in the current through the coil, which can be measured and used to sense properties of the propagated signal (including e.g. frequency spectrum, amplitude and phase pattern).

An electromagnetic excitation signal can be propagated into a body to be investigated. The excitation electromagnetic signal causes magnetic induction in the body, i.e. the generation of eddy currents in the tissue of the body due to the application of an external magnetic field. These eddy currents then in turn generate electromagnetic signals propagated out of the body which interact with the applied fields in a way that allows them to be sensed by the coil.

Movements of tissue in the body can manifest in changes in volumes of local regions of the tissue and in changes of the conductive or dielectric properties of a tissue. These changes then cause amplitude and/or phase modulations of the electromagnetic signal which is emitted out of the body in response to the electromagnetic stimulation. By monitoring these changes, movement and size change of elements within the body can be detected and tracked, and changes in the conductivity and dielectric properties can be tracked. For example, heart contractions manifest themselves mainly as movement of blood, and breathing mainly manifests itself as changes in the conductivity of the lung.

For 50 years, beginning with the first two papers in this field in 1967 (Vas et al) and 1968 (Tarjan et al.), this field has been an area of active research, multiple publications appearing each decade. One active aim in particular has been to obtain strong cardiopulmonary signals using an inductive sensor. Strong signals in general has been an aim.

The ongoing research however has never led to adoption of the technology in commercial applications, since the signals achieved from inductive sensors remain notoriously weak, and often saturated by noise.

Improving the strength of magnetic signals received from the body during inductive sensing is hence a very important area for development. In state of the art systems, signal strength remains prohibitively low, preventing the technology from being usefully applied in commercial applications.

It is an object of the present invention to improve the signal strength of detected electromagnetic signals received from a body during inductive sensing.

SUMMARY OF THE INVENTION

The invention is defined by the claims.

According to an aspect of the invention, there is provided a physiological parameter inductive sensing system for sensing electromagnetic signals emitted from a body in response to electromagnetic excitation signals propagated into said body, the system comprising:

a loop resonator for inductively coupling with said electromagnetic signals emitted from the body, the resonator comprising a loop antenna and an electrically coupled capacitor, the loop of the antenna having only a single turn of circumferential length l, and a signal generation means adapted to excite the resonator to generate the electromagnetic excitation signals having a radial frequency $\omega$ for propagating into said body, wherein a normalized radial frequency $$\hat{\omega} \equiv \frac{\omega}{\omega_{ref}}$$

of the electromagnetic excitation signals is from 0.025 to 0.50, where $\omega_{ref} = 2\pi c/l$ and c=the speed of light.

For the avoidance of doubt c=3×108 m/s.

The invention is based on results of a significant program of research undertaken by the inventors by which it has been found that the above parameter of normalized radial frequency $\hat{\omega}$ of the electromagnetic excitation signals is one of the most important parameters in determining the strength of the signal sensed by the system (as well as the absolute frequency f).

More particularly, research has found that at values of $\hat{\omega}$ below 0.025, the signal to noise ratio of the sensed electromagnetic signal is significantly reduced, leading to higher motion sensitivity. More particularly, below this level, the signal strength is much decreased, and in most practical applications saturated by noise emanating from electronic noise, electromagnetic interference and noise from capacitive coupling with the surface of the body (i.e. direct coupling via electric fields and electrically induced charges).

However, despite the highly significant signal strength advantages which the inventors have managed to achieve with this invention, frequencies as high as those claimed have never been explored in the state of the art. This is most likely due to a strong prevailing belief in the field that (absolute) frequencies above around 10-29 MHz lead to a significant reduction in achievable penetration depth due to skin effects. The assumed penetration depth reductions would render the system ineffectual for probing physiological parameters. The inventors however have found that this prevailing prejudice is a misconception, as even though the skin effect is real, it becomes only significantly detrimental at much higher frequencies than those used in the present invention.

It has further been found that a value of 0.50 for $\hat{\omega}$ is the highest that is physically possible while still achieving effective inductive sensing. This is the highest possible normalized frequency of the first resonance of a (single) loop antenna, which is the resonance at which precisely half a wavelength fits around the circumference of the loop.

Above the first resonance, a highly non-uniform current is induced in the loop of the resonator, and the loop will carry a stationary oscillating pattern of accumulated charges. This fringe pattern of accumulated charges will typically capacitively couple to the surface of the body, thereby inducing surface charges on the surface of the subject's skin.

In this case, the sensor is rendered highly sensitive to motion of the body surface, where even very small movements induce parasitic signals which fully drown out the inductive signal being sensed (namely the magnetic inductive signal originating from beneath the surface of the body). This renders the inductive sensor ineffective for most practical applications. Hence, by keeping $\hat{\omega}$ below a value of 0.5, signal strength can be maintained at a level suitable for practical applications.

The range of values for $\hat{\omega}$ provided by the present invention therefore maximise the signal strength achievable in magnetic inductive sensing.

It has further been found in the course of investigation that, contrary to expectation, increasing the number of coil windings (coil turns) N above one (a single loop) provides no detectable improvement in signal strength. Moreover, increasing the number of windings is in fact detrimental to the object of maximizing signal strength because increasing the number of windings limits the maximum realizable value of $\hat{\omega}$ due to capacitive coupling between the windings. This in turn restricts the available increase in signal strength.

The two features of the above defined $\hat{\omega}$ range and the single coil antenna are therefore fundamentally interrelated. Where the antenna comprises more than a single turn (N>1), the maximum frequency $\hat{\omega}$ that can be used with the loop is significantly reduced below $\hat{\omega}$=0.5 due to parasitic capacitances between the loops and the longer total length of the coil wire Nl. This makes achievement of the beneficial normalized frequency range claimed in the present invention, and the accompanying increases in signal strength, impossible. Hence, only by reducing the number of coil windings to one are the beneficial higher $\hat{\omega}$ values possible.

However, restricting the coil windings to one is contrary to prevailing assumptions in the art, which generally assume that multiple coil windings increases signal strength by enhancing the flux linkage. This has further contributed to the reluctance in the field to explore frequencies in the range presently claimed.

Multiple windings also add cost and complexity to the sensor. Reducing to a single loop simplifies construction and operation of the device and reduces form factor.

More detailed physical explanation and grounding of the particular range identified will be presented below. In brief however, the claimed invention is based on the finding that reflected inductance (inductance of the antenna resulting from eddy currents induced in the body in response to electromagnetic stimulation) is the key determinant in the resulting received signal strength at the antenna. By first normalizing this quantity, so as to render it effectively dimension-independent, and then simulating variation of various parameters upon which it is dependent, normalized radial frequency of the sensed signals was found to be the most significant parameter determining reflected inductance. The optimal range of values for $\hat{\omega}$ claimed in the present application was then identified based on modelling and experimentation.

The system of the present application is a physiological parameter inductive sensing system. The system is hence for sensing electromagnetic signals received from a body of a subject in response to electromagnetic excitation signals applied to the body of the subject.

The system may in particular be a vital sign sensing system. Vital signs may include for instance heart rate, pulse rate, breathing capacity, breathing rate, stroke volume, stroke volume variations, cardiac output, or aortic or arterial pulse height/pressure/diameter modulations.

It is noted that although the present application is directed to physiological parameter sensing, the inventive concept embodied by the invention is not in principle limited only to the measurement of physiological parameters (such as vital signs). The inventive concept is applicable more broadly to any inductive sensing system. Examples will be described in the next section.

Electromagnetic excitation signals having a radial frequency $\omega$ may be generated by exciting the resonator at a radial frequency of $\omega$. By this may be meant exciting the resonator so as to resonate at a frequency of $\omega$. By this may in particular be meant inducing in the antenna a resonating current having radial frequency $\omega$.

This may be achieved by providing a resonator having a natural resonance frequency equal to $\omega$. The natural resonance frequency of the resonator can be set by appropriately selecting the capacitance of the capacitor.

Additionally or alternatively, exciting the resonator so as to induce in the antenna a resonating current having radial frequency $\omega$ may be achieved by exciting the resonator with a current of frequency $\omega$.

The normalized radial frequency $\hat{\omega}$ of the electromagnetic excitation signals is dependent upon the radial frequency $\omega$ of the electromagnetic excitation signals and a reference frequency $\omega_{ref}=2\pi c/l$ of the antenna (which is the radial frequency at which the loop circumference l equals one free-space wavelength (i.e. where $\lambda_{free\ space}$=l)).

Hence embodiments of the invention may require that the antenna, capacitor and/or signal generation means are together configured such that the normalized radial frequency is within the defined range.

By way of example, this may be achieved for instance by providing a resonator having a capacitance selected such as to set the natural resonance frequency of the resonator at $\omega$, and choosing an antenna with the correct circumferential length l. Where the resonator has a given natural resonance frequency, it may be induced to resonate at that frequency by exciting it, for instance using a free-running oscillator (one without a fixed or forced oscillation frequency).

The system in accordance with the present application may be for sensing electromagnetic signals emitted from a body of a subject, i.e. a physiological, diagnostic or medical sensing system. However, the system is applicable more generally to sensing electromagnetic signals received from any body, where body is to be understood broadly as meaning any physical object or entity, or any region of such an object or entity.

The sensing system comprises a signal generation means for exciting the resonator to generate electromagnetic signals of a radial frequency ω for propagating into the body.

By exciting the resonator, a resonating current is induced to flow back and forth through the loop antenna into the capacitor.

The resonator may be excited by driving an (alternating) current through the antenna such as to stimulate generation of oscillatory electromagnetic signals (waves).

By driving the antenna at a current with frequency ω, electromagnetic excitation signals of frequency ω may be generated.

The signal generation means may comprise a driver means for driving the antenna, for instance at a radial frequency ω, i.e driving the antenna with an alternating current of frequency ω. The driving means may be oscillator for instance.

The same antenna is used to generate the excitation signals as is used to sense the electromagnetic signals received from the body in response.

For the avoidance of doubt 'electromagnetic excitation signals' simply means electromagnetic signals for propagating into the body for the purpose of exciting or stimulating generation of eddy currents within the body for in turn stimulating emission of electromagnetic signals back out of the body which can be sensed by the sensing system.

By 'electromagnetic signals' may generally be meant electromagnetic radiation emissions or electromagnetic oscillations and/or electromagnetic waves.

In accordance with one set of embodiments, the normalized radial frequency $\hat{\omega}$ of the excitation signals may be from 0.025 to 0.25

Within this range, current amplitude when sensing the signals received back from the body is substantially constant (homogeneous) over the antenna loop. Above $\hat{\omega}$=0.25, the current amplitude varies to a greater extent over the antenna loop. Phase of current is also relatively constant around the antenna loop. These factors are significant limiting factors in achieving high signal strength and high quality signal.

Inhomogeneous currents in particular are highly disadvantageous because these result in accumulated charges in the antenna loop which in turn lead to capacitive coupling with the medium being examined. Capacitive coupling with the medium is a primary source of signal distortion (motion artefacts) in inductive sensors.

In accordance with one set of embodiments, the normalized radial frequency $\hat{\omega}$ of the excitation signals may be from 0.025 to 0.20. Below an upper limit of 0.20 for $\hat{\omega}$, radiation resistance is kept optimally low (<0.5Ω), current phase is relatively constant over the antenna loop and uniformity of current amplitude is further improved (<20% difference in current amplitude between any two points around the loop).

This range is also particularly advantageous since above $\hat{\omega}$=0.20, some electrical effects begin to occur, resulting in the coil becoming sensitive to the electric field component of the electromagnetic (EM) signals received back from the body (which interferes with the sensitivity to magnetic field signals). Below $\hat{\omega}$=0.20, it has been found that the sensing system remains strongly inductively sensitive to the induced electromagnetic signals emerging from the body, without building up significant electrical charges along the single antenna loop wire.

In accordance with one set of embodiments the normalized radial frequency $\hat{\omega}$ of the excitation signals may be from 0.04 to 0.25. A lower limit of 0.04 is preferred since it results in higher signal strength (than 0.025 for instance) while still maintaining the benefits of very low radiation resistance (~0.01Ω), constant current phase over the antenna loop and constant current amplitude over the antenna loop.

It has been found that a normalized radial frequency $\hat{\omega}$ above 0.04 provides a signal of strength sufficiently high that the signal is reliably robust against noise across a wide range of practical applications. In certain scenarios (although not all), electromagnetic signals below this normalized frequency can become distorted by noise artefacts originating from capacitive coupling with the tissue surface (i.e., electric coupling with the surface of the body due to electrically induced charges). For conveniently-sized sensors of e.g. radius=1 to 3 cm, it has been found that signal strength is doubled compared to signals using normalized radial frequency of around 0.025. Breathing signals (signals indicating breathing function) have in particular been found to have significantly higher signal strengths. This will be explained in more detail in the next section.

As noted above, in examples, the signal generation means may be adapted to excite the resonator to resonate at a radial frequency ω in order to generate the excitation signals having radial frequency ω.

The resonator (circuit) may be provided having a natural radial frequency of ω in order to facilitate exciting of the resonator at a radial frequency of ω, and optionally wherein the capacitor is selected for tuning the natural radial frequency of the resonator to ω.

The system may comprise a signal processing means adapted to process signals received at the antenna. The signal processing means may be adapted to sense changes in a natural resonance frequency of the resonator (i.e. detuning of the resonator), and use these changes to derive a signal output. The signal processing means may additionally or alternatively sense changes in a damping factor of the resonator circuit and use these changes to derive a signal output.

Sensing of changes in the natural resonance frequency may be preferred because measuring damping factor changes requires measuring the imaginary part of reflected inductance which might require additional complexity in the circuitry of the signal processing means. However, measurement of the imaginary part, and hence the damping factor, is possible in accordance with one or more embodiments.

In accordance with at least one set of embodiments, the system may comprise a signal processing means adapted to process signals received at the antenna to downscale a frequency of the signals by mixing the signals with a reference oscillatory signal of a different frequency, and applying a differential filter to derive a signal having a frequency being the difference between the frequency of the reference oscillatory signal and the received signals.

The object of such embodiments is to reduce energy consumption and required computing power of any signal processing performed by the system. In particular, digital dividers and counters (for processing the received signals for analysis) draw current proportional with the operating frequency. Hence, to save power, in accordance with the present embodiments, the frequency of the received signals is first reduced, allowing the subsequent signal processing to be performed at lower power.

The advantage of the particular embodiment proposed, of first mixing a second signal and then finding a differential frequency signal, is that mixing does not result in a loss of resolution. This is contrast for instance to dividers (which can also be used to reduce frequency) which do reduce resolution. The invention is still compatible with use of dividers in other embodiments however.

The reference oscillatory signal frequency is preferably very close to the frequency of the received signals. In preferred examples, the frequency of the oscillatory signal and the frequency of the received signals are from 10 to 20% apart.

As explained above, the received signals will typically have frequency equal to $\omega$, i.e. the radial frequency of the electromagnetic excitation signals.

In accordance with one or more embodiments, the signal generation means may be adapted to control the antenna to generate electromagnetic excitation signals at a frequency of from 30 MHz to 1000 MHz.

The frequency here refers to absolute frequency f, rather than radial frequency $\omega$.

In accordance with these embodiments, an absolute frequency requirement is provided. Accordingly, since $$\hat{\omega} \equiv \frac{\omega}{\omega_{ref}} \text{ and } \omega = 2\pi f,$$

a corresponding requirement is imposed upon $\omega_{ref}=2\pi c/l$, meaning that the circumferential length l of the antenna loop must be configured to achieve the desired f. In particular, these embodiments require $l=\hat{\omega}c/f$.

Applying excitation signals to a body at such high frequencies is not known in the prior art. This is because it is commonly understood in the art that frequencies above around 30 MHz lead to significant reduction in achievable penetration depth, while increasing the required operating power. However, inventors of the present invention have found that the reduction in penetration depth does not become prohibitive to inductive sensing (in particular for physiological parameter sensing) until much larger frequencies are reached. This is particularly the case in applications pertaining to investigating breathing function. These embodiments hence improve signal strength, and with no prohibitive reduction in penetration depth.

This frequency range is beneficial because signal strength becomes significantly larger above f=30 MHz. This is particularly so for relatively smaller sized loops (radii in the range of 1-3 cm). In this case, where for instance the signal is measured by changes in resonance frequency of the resonator (as described above), the frequency shift signal (real part of reflected inductance) quickly becomes much stronger when going into this range, by both an increase in signal strength, and also a movement in the phase of the reflected inductance towards the real part.

This frequency range is also particularly advantageous when using a signal processing means in the form of a mixer-counter. The absolute changes in the resonator resonance frequency due to, for instance, breathing when using f<30 MHz can be below 1 kHz. When using a slope counter, the quantization noise of the number of counts in the signal is readily visible at this operating frequency.

When increasing the absolute frequency above f>30 MHz the influence of quantization noise on the signal will in most cases cease to be problematic. This is described in greater detail below.

In addition, it is beneficial to maintain frequency below 1000 MHz in order to optimize penetration depth. At frequencies above 1000 MHz, penetration depth of electromagnetic signals start to become prohibitively small for measuring physiological parameters, e.g. lung or heart signals.

In accordance with one or more embodiments, the signal generation means may be adapted to excite the resonator to generate electromagnetic excitation signals having a frequency of from 100 MHz to 1000 MHz.

At frequencies above 100 Hz, penetration depth is still sufficiently deep while signals become much stronger. Cardiopulmonary signals in particular have been found to become much stronger. In addition, the phase of the reflected inductance moves further toward the real part. This is beneficial where the signal generation means is adapted to measure changes in the resonator resonance frequency, which requires sensing the real part of reflected inductance.

In addition, above a frequency of 100 MHz, the quantization noise of e.g. a slope-counter signal processing means (at e.g. integration times of around 0.05 seconds) is almost negligible relative to the signal strength. This is described further below.

In accordance with one or more embodiments, the signal generation means may be adapted to excite the resonator to generate electromagnetic excitation signals having a frequency of from 30 MHz to 500 MHz.

This absolute frequency range optimizes penetration depth, in particular for muscle. The signal strength at 500 MHz remains very high, while penetration depth is maintained relatively large (~5 cm for muscle—and higher for other media).

This frequency range may also be preferred where power consumption is a concern, e.g. battery powered sensors. Below 500 MHz, the frequency is low enough that it does not significantly contribute to signal processing power consumption.

In accordance with one or more embodiments, the signal generation means may be adapted to excite the resonator to generate electromagnetic excitation signals having a frequency of from 100 MHz to 500 MHz.

This combines the benefits 100 MHz lower boundary and 500 MHz upper boundary discussed above.

Exciting the resonator to generate signals of the above frequencies can be performed in accordance with the example methods outlined above.

In particular advantageous examples, the loop of the antenna may have a radius of between 15 mm and 20 mm.

In further advantageous applications, the loop of the antenna may have a radius of between 90 and 110 mm.

Loop radii of 15 or 20 mm are desirable because larger loops have been found to be more sensitive to movement of objects in the environment since the distribution of the electromagnetic field scales proportionally with the loop size where the relative frequency is kept constant. Loops with radii smaller than 15 mm are possible, but the obtained signal strength decreases.

Antenna loops of radius between 90 and 110 mm are advantageous for instance in cases where sensing over a relatively long distance is required. For instance, an antenna of such a size may be embedded in a mattress or a chair, and allowing sensing through the materials of the furniture. An antenna loop having radius of 100 mm has been tested and found beneficial in such applications for instance.

In accordance with one or more embodiments, the system may comprise a processor for processing signals sensed by the antenna to derive one or more physiological parameters.

Examples in accordance with a further aspect of the invention provide a physiological parameter inductive sensing method comprising sensing electromagnetic signals emitted from a body in response to electromagnetic excitation signals propagated into said body, the method comprising:

exciting a loop resonator to generate the electromagnetic excitation signals and directing the signals into said body, wherein the resonator comprises a loop antenna and electrically coupled capacitor, the loop antenna having only a single-turn loop of circumferential length l; and using the loop resonator to inductively couple with the electromagnetic signals emitted from the body in response to the excitation signals, wherein a normalized radial frequency $$\hat{\omega} \equiv \frac{\omega}{\omega_{ref}}$$

of the electromagnetic excitation signals is from 0.025 to 0.50, where $\omega_{ref}=2\pi c/l$ and c=the speed of light.

All terms are to be interpreted in accordance with the discussions above in relation to the sensing system aspect of the invention.

In accordance with at least one set of embodiments, the method may comprise processing signals received by the antenna to derive physiological parameter information.

In accordance with one or more embodiments, the normalized radial frequency $\hat{\omega}$ of the electromagnetic excitation signals may be from 0.025 to 0.25.

Any of the options or embodiments outlined above in relation to the sensing system aspect of the invention may also be advantageously applied or incorporated into the present method aspect of the invention.

BRIEF DESCRIPTION OF THE DRAWINGS

Preferred embodiments of the invention will now be described in detail, by way of example only, with reference to the accompanying drawings, in which.

DETAILED DESCRIPTION OF THE EMBODIMENTS

Figure 1:
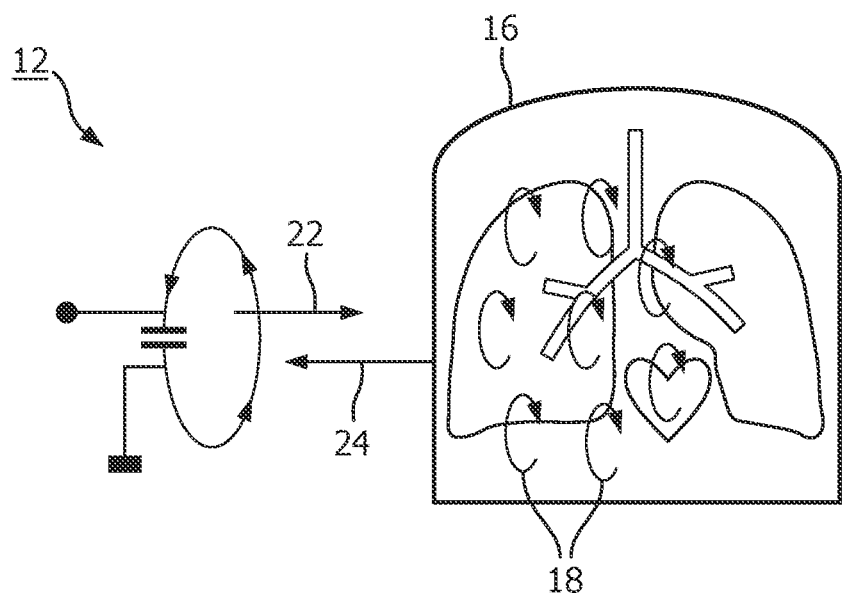
FIG. 1 shows stimulation of a thorax of a subject in the vicinity of a resonator consisting of a loop antenna and a capacitor.

The invention provides a magnetic inductive sensing system for sensing electromagnetic signals emitted from a body in response to electromagnetic excitation signals applied to the body. The electromagnetic signals are generated and sensed by the same loop resonator which comprises a single-turn loop antenna and a tuning capacitor. The loop antenna of the resonator and a signal generation means for exciting the resonator to generate excitation signals are together configured so as to optimize the value of a ratio between the radial frequency of the generated electromagnetic excitation signals and a reference frequency of the antenna, where the reference frequency is the frequency for which one wavelength of the generated excitation signals (waves) matches the circumferential length of the antenna. This ratio, which corresponds to a normalized radial frequency of the generated excitation signals, is maintained between a value of 0.025 and 0.50.

The invention is based on results of a research program undertaken by the inventors in which it was found that the normalized radial frequency $$\hat{\omega} \equiv \frac{\omega}{\omega_{ref}}$$

of the applied electromagnetic excitation signals is the key parameter in determining the strength of signals sensed by the antenna (where $\omega$ is the radial frequency of the excitation signals, $\omega_{ref}=2\pi c/l$, and l is the circumferential length of the single-turn loop of the antenna).

The theoretical underpinnings of the invention will now be explained with reference to FIGS. 1 to 5.

Embodiments of the invention operate on the principle of inductive coupling, whereby a coil or wire has induced across it a potential difference due to exposure to a time varying magnetic field. Embodiments of the present invention use this principle to measure strength of electromagnetic signals generated within regions of a body by sensing changes in the inductance of a coil placed in proximity to the body, where these changes are detected based on changing resonance characteristics of the coil circuit.

Any electrical conductor exhibits a property of self-inductance. Self-inductance is the property of an electrical conductor by which a change in the current being driven through the conductor results in induction of an electromotive force in the conductor. According to Lenz' law, the induced electromotive force is in a direction such as to resist the change in current which is inducing it. It is hence commonly termed 'back-EMF'. Self-inductance can be understood as arising due to a magnetic flux induced as a result of the change in current (Ampere's law). This flux then interacts with the conductor itself to induce a back-EMF (Faraday's law of induction and Lenz' law).

The relationship between self-inductance L of a circuit, the voltage, v(t), and the current I(t) can be expressed as:

$$v(t) = L \frac{dI(t)}{dt} \tag{1}$$

By using Faraday's law of induction to express v(t) as dΦB/dt (where ΦB is magnetic flux) and integrating with respect to time (assuming L to be time-constant), free-space self-inductance L for a coil of N turns can be expressed as:

$$L = N\Phi_B/I \tag{2}$$

Embodiments of the present invention make use of a resonator comprising a single turn loop antenna to stimulate or excite a body with electromagnetic signals (waves) and to sense signals emitted back from the body in response to those excitation signals.

The coil may be driven with an alternating current to generate the excitation signals for propagation into the body.

When the coil is brought into proximity with a body, the inductance L acquires an additional reflected inductance component, $L_r$, arising due to eddy currents induced in the stimulated body as a result of application of the excitation signals. This is illustrated schematically in FIG. 1, which shows by way of example a loop antenna 12 being driven with an alternating current in proximity to a thorax 16 of a subject, so as to propagate electromagnetic signals 22 into the thorax.

As a consequence, eddy currents 18 are induced within in the thorax. The eddy currents naturally arise due to Faraday's law of induction, whereby an electromotive force (EMF) is induced in a conducting medium in response to presence of a time-varying magnetic field.

These eddy currents in turn effectively make a contribution to the inductance of the loop antenna 12. This is because they themselves result in generation of a time-varying magnetic flux 24 of equivalent frequency to that generated by the primary antenna 12. These eddy-current fluxes combine with the primary flux of the antenna, resulting in a greater induced back-EMF in the antenna, and hence a larger measurable effective inductance.

The added component of inductance arising from the eddy currents is referred to as 'reflected inductance', $L_r$. The total inductance $L_t$ of the coil antenna 12 may be expressed as:

$$L_t = L_0 + L_r \tag{3}$$

where $L_0$ is the self-inductance of the coil antenna 12 and $L_r$ is the reflected inductance.

Reflected inductance can be defined as:

$$L_r \equiv \frac{1}{I} \oint_{all\,turns} A_r \cdot dl \tag{4}$$

where $A_r$ is the reflected part of the electromagnetic vector potential (i.e. the part that is generated by the eddy currents 18 in the stimulated medium), and I is the coil current. The reflected inductance is closely related to the reflected impedance $Z_r$. The relationship is $L_r = Z_r/i\omega$, where ω is the radial frequency of the electromagnetic excitation signals 22 (the time-varying field applied to the body).

The above integral expression can be understood by applying the relationship:

$$\nabla \times A_r = B_r \tag{5}$$

where $B_r$ is the 'reflected' magnetic field and then applying Stokes' theorem to re-express equation (4) as:

$$L_r \equiv \frac{N}{I} \int\!\!\int_s B \cdot ds = \frac{N\Phi_B}{I} \tag{6}$$

where N=number of turns. It can be seen that this corresponds to the form of the simplified expression for inductance outlined in equation (2) above.

The magnitude of the reflected inductance component gives an indication of the strength of the 'reflected' electromagnetic signals emitted back from the body. Stronger signals give higher signal to noise ratio, which improves the quality and reliability of the sensed signals. By seeking to optimize the strength of Lr, the signal to noise ratio may thereby be maximized.

In general, the reflected inductance, $L_r$, is complex, and can be expressed as $$L_r = L'_r + iL''_r \tag{7}$$

where $L'_r$ is related to a reactive impedance of the coil antenna and $L''_r$ is related to resistive impedance of the coil.

The addition of the reflected component of inductance $L_r$ leads to a detuning of the characteristics of the coil. In particular, both the natural radial frequency of the coil antenna circuit and the damping factor of the coil antenna circuit change. By measuring this detuning of the coil characteristics, the magnitude of the reflected inductance $L_r$ can be determined, and the reflected signals measured.

In particular, the detuning of the characteristics of the coil as result of the addition of the reflected inductance can be expressed as follows:

$$\omega_{0,t} = \omega_{0,0} \sqrt{\frac{L_0}{L_0 + L'_r}} \tag{8}$$

$$\zeta_t = \zeta_0 \sqrt{\frac{L_0}{L_0 + L'_r}} + \frac{-L''_r}{2(L_0 + L'_r)} \tag{9}$$

where $$\omega_{0,0} = \sqrt{\frac{1}{CL_0}}$$

is the undamped natural radial frequency of the coil circuit in free space, $\omega_{0,t}$ is the natural undamped radial frequency of the coil circuit in the presence of a medium or body (the subscript t standing for 'total'), $$\zeta_0 = \frac{\frac{R_0}{\omega_{0,0}}}{2L_0}$$

is the damping factor in free space, $\zeta_t$ is the (total) damping factor in the presence of a medium, $L'_r$ is the real part of the reflected inductance defined in equation (7) and $L''_r$ is the imaginary part of the reflected inductance defined in equation (7).

It can be seen that the detuned natural radial frequency depends only on the real part of the reflected inductance $L'_r$. The detuned damping factor depends also upon the imaginary part of the reflected inductance $L''_r$.

For simplicity, it is preferable to work with geometrically normalized quantities. Accordingly, a 'characteristic' self-inductance $\hat{L}_0$ and reflected inductance $\hat{L}_r$ can be defined as follows:

$$\hat{L}_0 \equiv \frac{L_0}{lN^2} \quad (10)$$

$$\hat{L}_r \equiv \frac{L_r}{lN^2} \quad (11)$$

where l=circumference of a single turn of the coil, N=number of coil windings, $L_0$ is free-space self-inductance (real), $L_r$ is reflected inductance (complex), and where $L_r$ is defined as in equation (4) above. The benefit of using the geometrically normalized quantities lies in the fact that $\hat{L}_0$ is independent of system size and the number of turns in the antenna coil.

Using these characteristic quantities, the detuning of the characteristics of the coil as a result of the addition of the reflected inductance can be expressed as follows:

$$\omega_{0,t} = \omega_{0,0}\sqrt{\frac{\hat{L}_0}{\hat{L}_0 + \hat{L}'_r}} \quad (12)$$

$$\zeta_t = \zeta_0\sqrt{\frac{\hat{L}_0}{\hat{L}_0 + \hat{L}'_r}} + \frac{-\hat{L}''_r}{2(\hat{L}_0 + \hat{L}'_r)} \quad (13)$$

where $$\omega_{0,0} = \sqrt{\frac{1}{CL_0}}$$

is the undamped natural radial frequency of the coil circuit in free space, $\omega_{0,t}$ is the natural undamped radial frequency of the coil circuit in the presence of a medium or body (the subscript t standing for 'total'), $$\zeta_0 = \frac{\frac{R_0}{\omega_{0,0}}}{2L_0}$$

is the damping factor in free space, $\zeta_t$ is the (total) damping factor in the presence of a medium, $\hat{L}'_r$ is the real part of the characteristic reflected inductance defined in equation (9) and $\hat{L}''_r$ is the imaginary part of the characteristic reflected inductance defined in equation (9).

These equations have not been derived before and have allowed the inventors to derive novel physical insights, since these quantities provide signal strength measurement factors independent of both the loop radius and the number of coils in the antenna.

For instance, for circular loops in particular, typical values of the characteristic self-inductance are about 500-1100 nH/m, independent of the number of turns and the loop radius. To compute signal strength, it is only necessary to derive the value of a single variable, namely $\Delta\hat{L}_r$. More fundamental physical insights have hence been possible.

It can be seen from the above that the natural radial frequency of the system changes when in the presence of a medium by a factor which is dependent upon the real part of the reflected inductance $L_r$ and the damping factor changes in the presence of a medium by a factor which is dependent upon the imaginary part of the reflected inductance $L_r$. These changes can be used to sense $L_r$ and thereby determine a measure of the strength of the electromagnetic signals received from the medium (from the body being stimulated and sensed).

The inventors of the present invention have achieved improvement in the strength of the sensed signals through derivation of a novel and powerful expression for the reflected inductance which allows it to be quantitatively understood in a new way in terms of properties of the system which can be readily adjusted and optimized.

In particular, starting from equation (4) above, and restricting to cylindrical symmetry (appropriate for a coil antenna used in embodiments of the present invention), the reflected inductance becomes:

$$L_r = \frac{2\pi a N A_{r,\varphi}}{I} \quad (14)$$

where $A_{r,\varphi}$ is the azimuthal component of reflected vector potential, a is the radius of the coil antenna loop(s), N is the number of windings of the coil, and I is the coil current.

Using calculations for $A_{r,\varphi}$ set out in Cheng, D. H. S. (1965), The reflected impedance of a circular coil in the proximity of a semi-infinite medium, *IEEE Transactions on Instrumentation and Measurement*, 14(3), 107-116, the following expression for characteristic reflected inductance has been derived by the inventors:

$$\hat{L}_r = \mu_0 a \int_0^\infty \frac{J_1^2(\xi a) e^{-\kappa h} \Gamma(\xi) \xi}{\kappa} d\xi \quad (15)$$

where $\kappa \equiv 2\sqrt{\xi^2 - k_0^2}$ and $k_0^2 \equiv \omega^2 \mu_0 \varepsilon_0$, a is the radius of the loop, h is the distance from the loop to the medium, $J_1(x)$ is the first order Bessel function of the first kind, $\omega$ is the radial frequency of the electromagnetic waves (signals), $\Gamma(\xi)$ is the TE (i.e. s-polarized) Fresnel reflection coefficient of the (multilayer) structure being stimulated, and where $\xi$ is the transverse wavenumber within that medium.

Calculation of TE Fresnel reflection coefficients for a given medium is described in detail on page 186 of the book "Electromagnetic Waves and Antennas" by Sophocles J. Orfanidis (available online at: http://www.ece.rutgers.edu/~orfanidi/ewa/).

Since equation (15) shows that $\hat{L}_r$ is completely independent of the number of turns, and since (as shown earlier) $\Delta\hat{L}_r$ is representative of the signal strength, it can hence be seen that signal strength does not depend directly upon the number of coils. From this it can readily be seen that increasing the number of coils in the antenna has no beneficial effect on the signal strength.

The understanding of the reflected inductance represented by the above equation (15) has not been derived before. This approach allows a powerful quantitative understanding of the reflected signal strengths.

The reflected inductance of a system of a loop antenna above a homogeneous medium can be characterized in terms of five primary geometrical properties. These are: loop radius, a, frequency of electromagnetic signals/waves, ω, distance between loop and medium, permittivity of the medium and conductivity of the medium.

These can be understood as geometrical properties since they relate to five length scales within the system. Considering the case that the medium is a region of a subject's body, these can be understood as: loop radius, free-space wavelength of the EM waves, distance between the loop and the medium, EM wave wavelength inside the medium, and skin depth. It is noted that although N may be regarded as a coil property, it is not a geometrical property because it does not affect any of these five length scales.

All five length scales can be scaled by a factor x such that the resulting fields and eddy currents are also just a scaled copy. The resulting reflected inductance is then also scaled by a factor x, since the fields remain the same, while the loop circumference is increased by a factor x.

The characteristic reflected inductance $\hat{L}_r$ however remains unaltered since the scaling factor appears in both $L_r$ and l, and so cancels out (see equation (11) above).

The way in which the geometrical properties need to be scaled to describe an overall size increase by a factor x is indicated below.

| | | | |
|---|---|---|---|
| a | loop radius | → | ax |
| ω | radial frequency of generated EM signals | → | ω/x |
| h | distance from coil to medium | → | hx |
| ε | permittivity | → | ε |
| σ | conductivity | → | σ/x |
| $L_r$ | reflected inductance | → | $L_r$x |

Normalized geometrical properties can be defined which remain unchanged upon an overall size increase of factor x. These are defined below. These allow computation of the characteristic reflected inductance using just four parameters instead of five (for a homogeneous medium). This reduces the complexity of the present model for how system properties affect the signal strength.

Normalized Radius of Loop Antenna:

$$\hat{a} \equiv \frac{a}{a} = 1$$

Normalized Radial Frequency of Electromagnetic Excitation Signals:

$$\hat{\omega} \equiv \frac{\omega}{\omega_{ref}} = \left[\frac{\omega}{c/a}\right]_{circular\ coil} = \left[\frac{\omega}{2\pi c/l}\right]_{arbitrarily\ shaped\ coil}$$

Normalized Distance Between Loop Antenna and Medium: $\hat{h}$ $$\hat{h} = h/a$$

Normalized Permittivity:

$$\hat{\varepsilon} = \varepsilon$$

Normalized Conductivity:

$$\hat{\sigma} = \left[\frac{\sigma}{\varepsilon \omega_{ref}}\right]_{circular\ coil} = \left[\frac{\sigma l}{2\pi \varepsilon c}\right]_{arbitrarily\ shaped\ coil}$$

Normalized (Characteristic) Reflected Inductance:

$$\hat{L}_r \equiv \frac{L_r}{2\pi a N^2} = \frac{L_r}{l N^2}$$

In the above expressions, a is radius of the loop antenna, l is circumferential length of a single winding of the loop antenna and $\omega_{ref}=c/a=2\pi c/l$ is the radial frequency for which a single free-space wavelength of the EM signals is equal to the circumferential length l of the coil. In general, this is $\omega_{ref}=2\pi c/l$ (derived by setting λ=l in the general relation for free space waves ω=2πc/λ). In the special case of a circular coil, l=2πa, allowing simplification to $\omega_{ref}=c/a$.

Hence these normalized geometrical parameters allow the characteristic reflected inductance to be expressed in terms of 4 instead of 5 parameters, by rendering all quantities independent of the antenna loop radius. Normalized radial frequency $\hat{\omega}$ of the generated excitation signals is one of these parameters.

Through a number of computational models, the inventors have found that the parameter $\hat{\omega}$ is the strongest determinant of the strength of the measured characteristic reflected inductance $\hat{L}_r$.

Figure 2:
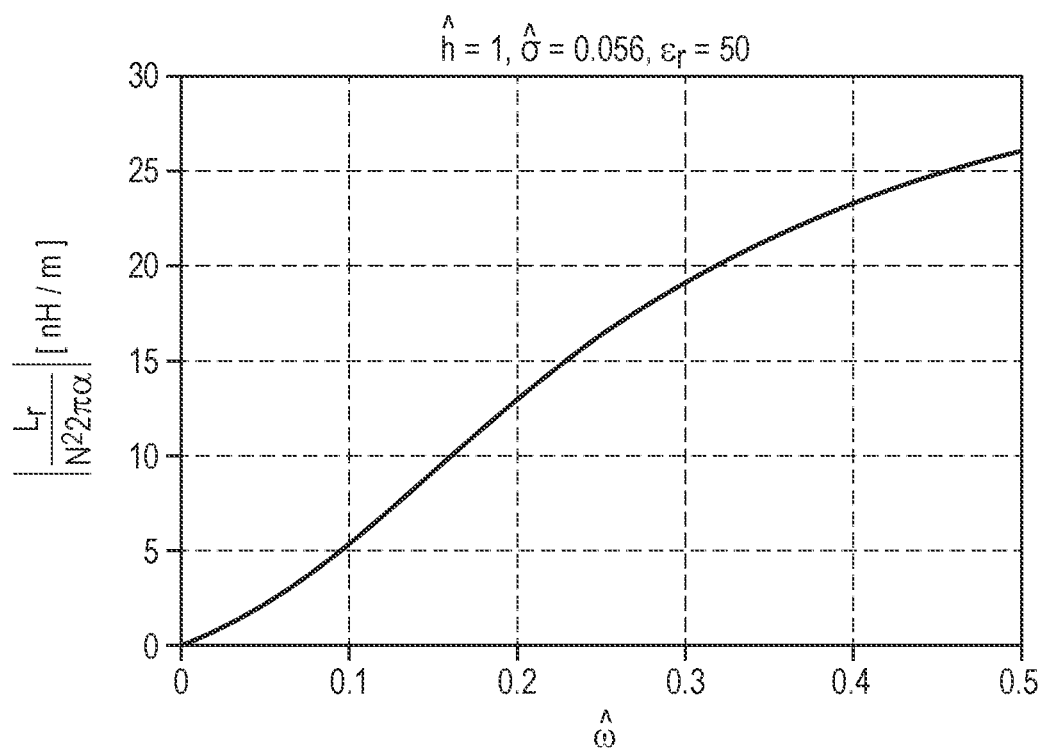
FIG. 2 shows dependency of characteristic reflected inductance on normalized radial frequency of electromagnetic excitation signals modelled for a homogeneous medium.

FIG. 2 shows results of computational modelling of electromagnetic stimulation of a homogeneous medium using a single turn (N=1) coil of fixed radius a, at a fixed characteristic distance from the medium $\hat{h}$=1, with fixed characteristic conductivity $\hat{\sigma}$=0.056 and fixed relative permittivity $\varepsilon_r$=50. The results show variation in strength of characteristic reflected inductance $$\hat{L}_r \equiv \frac{L_r}{2\pi a N^2}$$

for varying $$\hat{\omega} = \frac{\omega}{\omega_{ref}}.$$

It can be seen from the graph of FIG. 2 that there is a strong dependency in this simple homogeneous model of $\hat{L}_r$ upon $\hat{\omega}$. This was moreover found to be the strongest dependency of $\hat{L}_r$ upon any of the parameters $\hat{h}$, a, $\hat{\sigma}$ or $\varepsilon_r$.

This strong dependency was found to be replicated also in more complex models.

Figure 3:
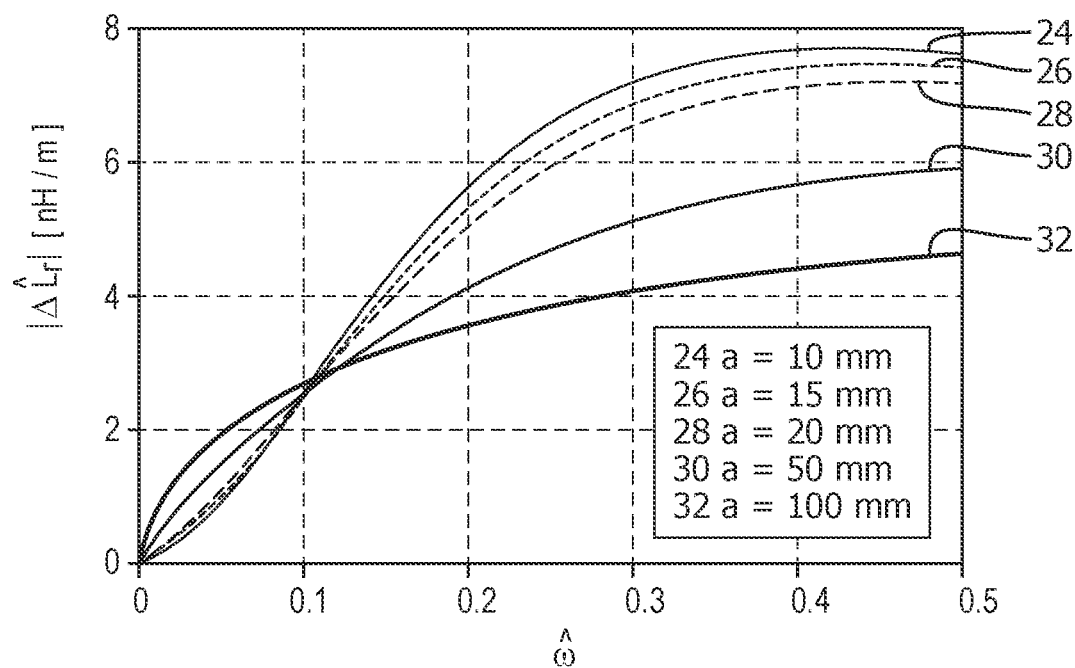
FIG. 3 shows dependency of the breathing component of characteristic reflected inductance on normalized radial frequency of electromagnetic excitation signals modelled for a bare lung.

FIG. 3 shows results of computational modelling for $\hat{L}_r$ as a function of $\hat{\omega}$ for a model constructed to represent a bare lung, by which is meant a lung by itself, in isolation of any layers of fat, muscle or bone which in practice surround it. For this model, the change in characteristic reflected inductance $\Delta \hat{L}_r$ between the lung when inflated and the lung when deflated $\Delta \hat{L}_r = L_r$ (inflated)−$L_r$ (deflated) was modelled as a function of $\hat{\omega}$. This change in $\hat{L}_r$ is a significant physiological parameter since it allows determination of characteristics of lung function.

Variation of $\Delta \hat{L}_r$ as a function of $\hat{\omega}$ was modelled for a single-turn loop antenna of five different radii a, ranging from 10 mm to 100 mm. Individual lines 24-32 are shown on the graph corresponding to the different radius sizes, with the radius size for each line indicated by the key in the graph.

It can be seen that there is a strong dependency of $\Delta \hat{L}_r$ upon $\hat{\omega}$ and, again, $\hat{\omega}$ was found to be the parameter upon which $\Delta \hat{L}_r$ was most strongly dependent.

Further to the bare lung model, a further model was computed for a multilayer lung, taking into account layers of fat, muscle and bone which surround the lung. Dependency of $\Delta \hat{L}_r = L_r$ (inflated)–$L_r$ (deflated) upon changing $\hat{\omega}$ was again calculated for this multilayer lung model.

Figure 4:
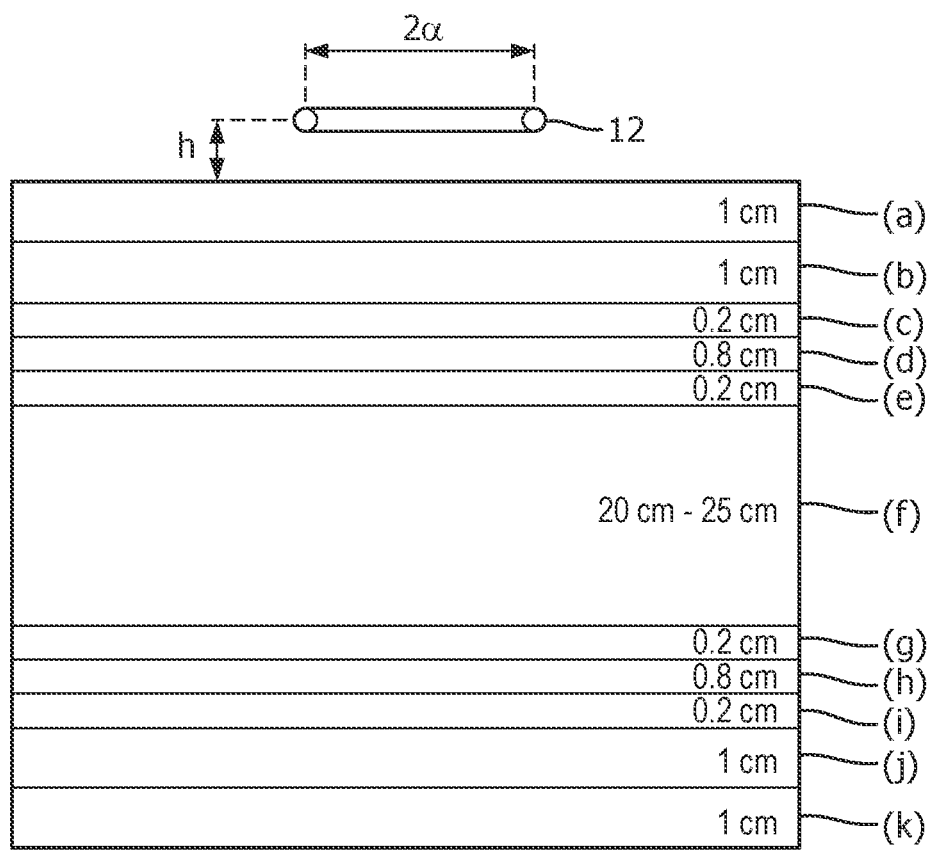
FIG. 4 shows the structure of a modelled multilayer lung.

A schematic illustration of the physical structure of the modelled multilayer lung is shown in FIG. 4. The lung itself is shown as layer (f) with a modelled height of 20 cm when deflated and 25 cm when inflated. Layered atop the lung are three bone layers: bone cortical (c), bone cancellous (d) and bone cortical (e) of 0.2 cm, 0.8 cm and 0.2 cm in height respectively. Atop the bone layers are an upper a layer of fat (a) of height 1 cm and an underlying layer of muscle (b) of 1 cm. Beneath the lung are also modelled three bone layers bone cortical (g), bone cancellous (h) and bone cortical (i) of 0.2 cm, 0.8 cm and 0.2 cm in height respectively, and a further layer of muscle (j) of 1 cm and layer of fat (k) of 1 cm.

The single-turn loop antenna of radius a is shown positioned at a distance h from the multilayer structure.

Figure 5:
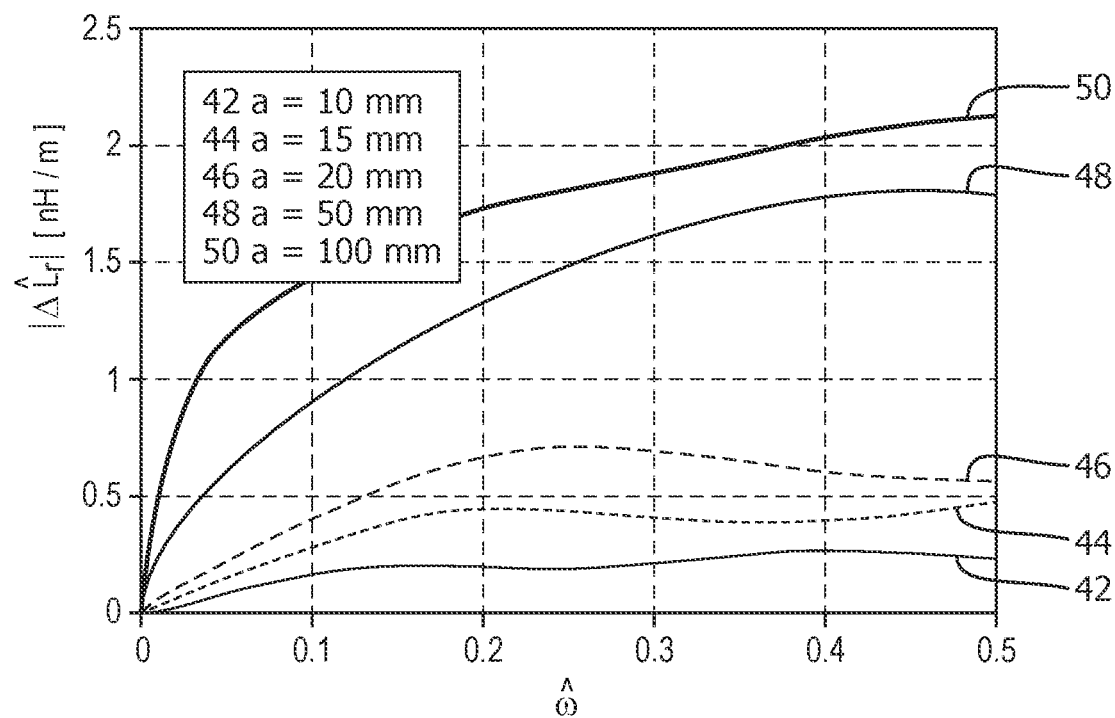
FIG. 5 shows dependency of the breathing component of characteristic reflected inductance on normalized radial frequency of electromagnetic excitation signals modelled for the multilayer lung of FIG. 4.

The results of the multi-layer lung model are shown in FIG. 5. Values for $\Delta \hat{L}_r$ as a function of $\hat{\omega}$ were derived for antenna of a range of different antenna coil radii a, varying from 10 mm to 100 m, with each of lines 42-50 corresponding to the derived result for one of the radii sizes, as indicated by the key in FIG. 5.

It can be seen that the strong dependency of $\Delta \hat{L}_r$ upon $\hat{\omega}$ remains present in the multilayer model for all of the radius sizes, although the radius of the coil does now make a non-trivial difference to the derived trend. However, as for the other more basic models, $\hat{\omega}$ was found to be the most significant factor in determining $\Delta \hat{L}_r$, with the relationship between $\Delta \hat{L}_r$ and $\hat{\omega}$ being stronger than with any other parameter.

Based on the derived model results, it can be determined that optimizing $$\hat{\omega} = \frac{\omega}{\omega_{ref}},$$

where $\omega$ is the radial frequency of the generated electromagnetic signals (the frequency at which the coil resonator is driven or excited) and $\omega_{ref}$ is the frequency for which a single free-space wavelength is equal to the circumferential length of the coil, represents the most effective approach to optimizing the strength of the sensed reflected inductance $\hat{L}_r$, and therefore optimising signal to noise ratio (signal strength).

The results show that in general higher $\hat{\omega}$ results in higher sensed magnitude of $\hat{L}_r$. However, the maximum $\hat{\omega}$ which is physically possible while still achieving effective inductive sensing has been found to be $\hat{\omega}=0.5$. This is because this is the half-wavelength resonance frequency of the loop (i.e. the maximum self-resonance frequency).

Above this frequency, a highly non-uniform current is induced in the loop of the resonator, and the loop will carry a stationary oscillating pattern of accumulated charges. This fringe pattern of accumulated charges will typically capacitively couple to the surface of the body, thereby inducing surface charges on the surface of the subject's skin.

In this case, the sensor is rendered highly sensitive to motion of the body surface, where even very small movements induce parasitic signals which fully drown out the inductive signal being sensed (namely the magnetic inductive signal originating from beneath the surface of the body). This renders the inductive sensor ineffective for most practical applications. Hence, by keeping $\hat{\omega}$ below a value of 0.5, signal strength can be maintained at a level suitable for practical applications.

It has also been found that below a value of $\hat{\omega}=0.025$, in addition to very low signal strength (as can be seen in FIGS. 2, 3 and 4), the sensitivity of the coil to electrical components of the electromagnetic signals becomes much increased. Due to the decreased signal strength, signal to noise ratio is significantly recued. As a result, the signal is in most practical applications effectively saturated by noise emanating from electronic noise, electromagnetic interference and noise from capacitive coupling with the surface of the body (i.e. direct coupling via electric fields and electrically induced charges).

Furthermore, modelling performed using all three model approaches (homogeneous medium, bare lung and multilayer lung) was found to demonstrate that increasing the number of windings of the coil N above one has no effect upon the characteristic reflected inductance $\hat{L}_r$ (and hence upon the signal strength). This is an unexpected result and is not currently known or utilised in the prior art. In prior art devices and methods, it is typically assumed that increasing the number of windings N will increase the achieved signal strength.

The independence of $\hat{L}_r$ to N can be seen directly in equation (15) above which shows that $\hat{L}_r$ has no dependency on N. This finding has hence emerged due to novel derivation of equation (15) by the inventors.

Moreover, not only does N have no positive effect upon signal strength, it is in fact detrimental to improving signal strength, since it limits the maximum physically realizable $\hat{\omega}$ due to capacitive coupling between the windings. Hence by increasing N, maximization of $\hat{\omega}$ is restricted. In addition, even at lower normalized frequencies, there is induced capacitive coupling between windings of a multi-turn coil which make the loop sensitive to capacitive coupling with the tissue. This in turn leads to distortions in the measured signal in the event of even small amounts of motion with respect to the skin. These motion artefacts can easily dominate the desired inductive signal, diminishing the efficacy of the sensor.

In addition, at high frequencies, the capacitive couplings between the turns will exhibit resonances that are very sensitive to detuning and these can greatly distort the targeted inductive sensing signal.

Based on the above three conclusions, in accordance with a first set of embodiments of the invention, there is provided a magnetic inductive sensing system for sensing electromagnetic signals emitted from a body in response to propagation into the body of electromagnetic excitation signals, where the system comprises a resonator comprising a loop antenna formed of a single-turn loop (N=1) of circumferential length l and wherein the resonator is excited to generate the excitation signals with a normalized radial frequency $$\hat{\omega} = \frac{\omega}{\omega_{ref}}$$

of from 0.025 to 0.50, where $\omega_{ref}=2\pi c/l$ and c=the speed of light.

Figure 6:
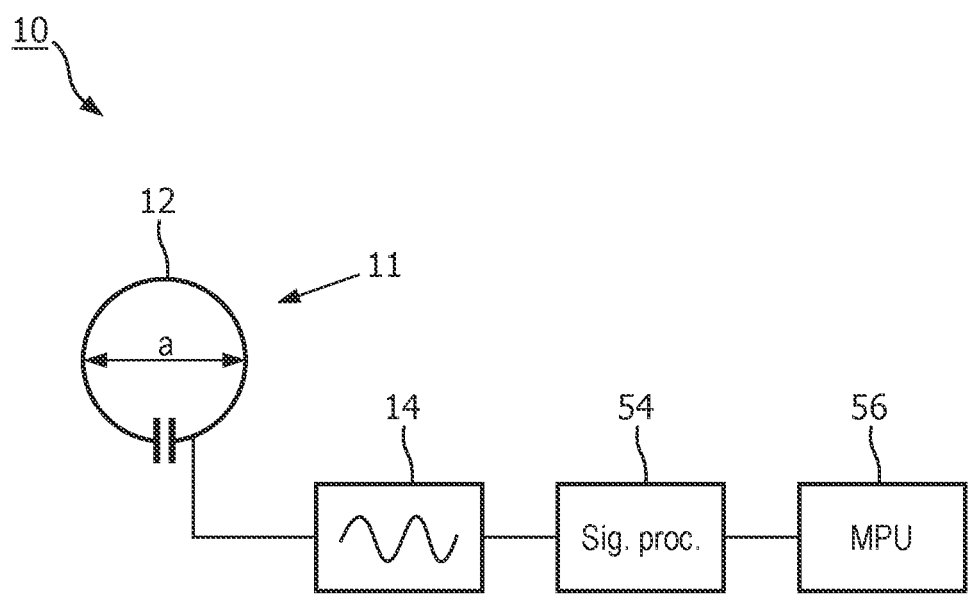
FIG. 6 shows an example sensing system in accordance with an embodiment.

An example magnetic inductive sensing system in accordance with one embodiment of the invention is schematically depicted in FIG. 6.

The system 10 comprises a loop resonator 11 comprising a single-turn loop antenna 12, the antenna being electrically coupled with a capacitor. The antenna is for generating electromagnetic oscillations or signals for propagation into a body and for inductively coupling with electromagnetic signals returned (or reflected) from the body in response to the excitation signals. The capacitor allows for tuning of a natural resonance frequency of the resonator circuit. When the resonator is then excited, it will naturally resonate at this frequency, generating electromagnetic signals at the same frequency. Selecting the capacitance of the capacitor hence allows for selecting the frequency of the generated electromagnetic signals.

The resonator 11 is electrically coupled to a signal generation means 14 which is adapted in use to excite the antenna to generate the electromagnetic excitation signals. In accordance with the present example, the signal generation means is an oscillator which is configured to drive the antenna 12 with an oscillatory current in order thereby to generate a sinusoidal electromagnetic signal (a sinusoidal electromagnetic wave) for propagation into the body to be stimulated.

The resonator 11 is further electrically coupled to a signal processing means 54 ('Sig Proc.') in the form of a signal processing unit for processing the electromagnetic signals received at the antenna 12. In FIG. 6, the signal processing means is shown connected to the resonator via the signal generation means 14. However, this is not essential: the resonator and signal processing means may be independently connected.

The signal processing unit 54 analyses the characteristics of the response signal received at the antenna 12. In particular, the signal processing unit may process received signals to derive a measure of changes in the damping factor of the resonator 11 circuit and the natural resonance frequency of the resonator signal. For the present example, the signal processing unit will be assumed to derive a measure of change in the natural resonance frequency only. This function will be described in greater detail below.

The system 10 also comprises a microcontroller 56 ('MPU') for controlling components of the system. For instance, the microcontroller may control the particular drive scheme implemented by the signal generation means 14 in exciting the resonator and/or the particular analysis processes implemented by the signal processing means 54 and/or may control the sequence of driving and analysis operations.

There may further be provided data communication means (not shown in FIG. 6) for facilitating communication between the microcontroller and an external device such as an external computer or data store. This may facilitate communication of signal processing results derived by the signal processing means to an external computer. It may also facilitate communication of control commands to the microcontroller 56 from an external control means such as a computer.

The data communication means may comprise a wireless communication means or wired communication means. The communication means may implement or operate in accordance with any suitable communication protocol or medium such as for example Bluetooth, Wi-Fi, Near Field Communication (NFC), ZigBee, or any suitable wired communication protocol.

The system 10 is configured to generate electromagnetic excitation signals of a normalized radial frequency $$\hat{\omega} = \frac{\omega}{\omega_{ref}}$$

of from 0.025 to 0.50, where $\omega_{ref}=2\pi c/l$, c=the speed of light ($3 \times 10^8$ m/s), and l is the circumferential length of the antenna loop. The normalized radial frequency $\hat{\omega}$ hence depends upon both the circumferential length of the antenna l and upon the radial frequency $\omega$ at which the resonator 11 is operated (the frequency at which it is excited).

For an antenna of fixed circumferential length l for instance, this requires that the resonator is excited at a radial frequency between $\omega=0.0125 l/\pi c$ and $\omega=0.25 l/\pi c$.

Exciting the resonator at a given frequency $\omega$ can be realised by selecting the capacitance of the capacitor such that a natural resonant frequency of the resonator 11 is equal to $\omega$. When the signal generation means (e.g. oscillator) then excites the resonator, it will resonate at a radial frequency $\omega$, thereby generating excitation signals of frequency $\omega$.

In the case of a circular loop antenna of radius a, l is naturally equal to $2\pi a$.

In use, the antenna 12 is held in proximity to a body or medium of interest, and the antenna is excited by the signal generation means 14 to generate electromagnetic excitation signals of a normalized radial frequency $$\hat{\omega} = \frac{\omega}{\omega_{ref}}$$

of from 0.025 to 0.50.

Advantageously, the system is used for sensing physiological parameters and properties, for instance air, fluid and/or tissue movements in the body of a subject. The system may sense vital signs. The system may be advantageously applied in particular for sensing breathing movements for instance.

In these examples, the system senses air, fluid and/or tissue movements (e.g. caused by breathing or the beating of the heart) by sensing modulations in the reflected inductance of the signal caused by these movements.

It will be appreciated that movements of tissue in the body can comprise changes in the volume of the tissue, as well as in the dielectric and conductive properties. These modulations cause amplitude and/or phase modulations of the electromagnetic signal.

A modulated electromagnetic signal is emitted by the body in response to an electromagnetic excitation signal that is emitted into the body of the subject. As described above, and illustrated in FIG. 1, the electromagnetic excitation signal causes magnetic induction, i.e. the generation of eddy currents 18 in the tissue due to the application of an external magnetic field 22, and this eddy current/electromagnetic signal is modulated by the movements of air, fluid and/or tissue in the subject.

The electromagnetic excitation signal is generated by means of the antenna 12 of the resonator 11, and the reflected electromagnetic signals (caused by the induced eddy currents) are sensed by the same antenna. This electromagnetic excitation signal is generated through exciting of the resonator by the signal generation means 14.

Magnetic fields penetrate deeper into a body than electrical fields, and thus magnetic fields can be used to measure changes in properties deeper inside the body, whereas electrical fields can be used to measure changes in properties on the surface of the skin, e.g. the permittivity of the skin. Thus, properties of the antenna 12 and the generated electromagnetic excitation signals are preferably configured such that the resonator and antenna is most sensitive to magnetic signals (magnetic components of the electromagnetic signals) and minimally sensitive to the electric signals, i.e. such that the magnetic field behavior of the emitted electromagnetic signal dominates over the electric field behavior.

Processing of the electromagnetic signals received from the body in response to the excitation signals may be performed in a number of ways.

As noted above, measurement of signals may be performed based on sensing detuning of characteristics of the resonator circuit. In particular, sensing can be performed by measuring changes in (1) undamped, natural radial frequency, and (2) the damping factor of the resonator circuit. The changes in these properties were expressed in equations (8) and (9) and (12) and (13) above.

Changes in one or both of these parameters can be used to sense received (reflected) signals.

The damping factor is dependent both on real and imaginary parts of the reflected inductance, whereas the natural frequency is dependent only on the real parts. It may be preferable in certain cases to sense just the real part, since sensing of the imaginary part (relating to damping) might require additional circuitry which might add complexity and cost to the system.

Particular examples will now be presented of signal processing means which make use of measuring of changes in the natural resonance frequency of the resonator.

In accordance with a first set of embodiments, the signal processing means may be implemented by a phased locked loop. An example of a phased locked loop circuit which may be used in accordance with this set of embodiments is shown in FIG. 7.

In this embodiment, a phase locked loop (PLL) is used to drive the resonator 11, and a control signal for the PLL provides an output signal representing the movement of air, fluid and/or tissue in the body of the subject. Hence, the circuit of FIG. 7 implements the functionality of both the signal generation means 14 and the signal processing means 54 of the example system of FIG. 6.

Figure 7:
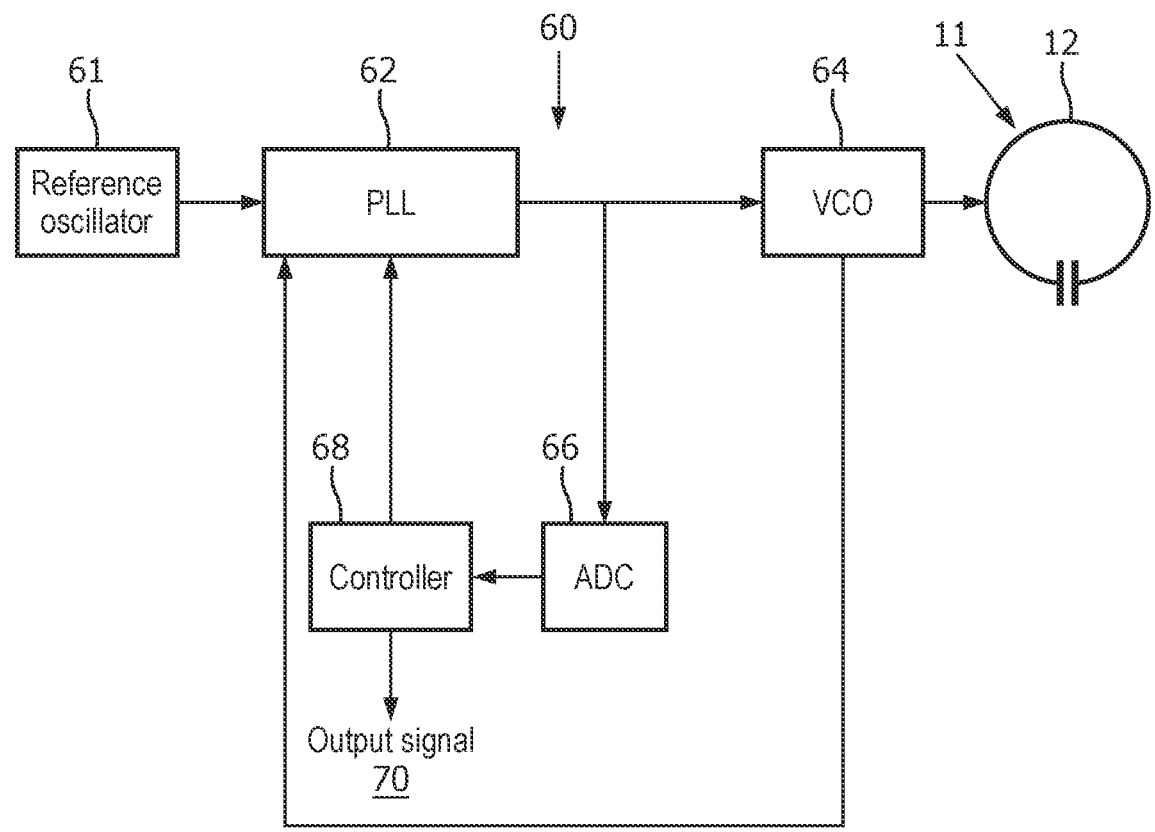
FIG. 7 shows an example sensing system processing circuit in accordance with an embodiment.

FIG. 7 shows signal generation and processing circuitry 60 for the resonator 11, and comprises a reference oscillator 61, a PLL 62 that is connected to the reference oscillator 61 and that outputs an analog control signal (known as $V_{tune}$) to a voltage-controlled oscillator (VCO) 64. The $V_{tune}$ signal is a result of a comparison of the signal from the reference oscillator 61 to the signal from the VCO 64. In response to the PLL analog control signal the VCO 64 generates an excitation signal at a required frequency and provides this to the resonator 11 so that the antenna 12 of the resonator 11 emits the electromagnetic excitation signal(s). As noted above the electromagnetic excitation signal will induce eddy currents in the body of the subject, and these eddy currents will induce a magnetic flux which is sensed by the antenna 12. This generated flux results in a reflected inductance component $L_r$ in the inductance of the antenna coil (as explained in detail above). This can be sensed via detuning of characteristics of the coil, in particular the natural frequency of the coil.

The excitation signal is also provided to the PLL 62 as part of a feedback loop. The analog control signal from the PLL 62 is also provided to an analog-to-digital convertor (ADC) 66 which converts the analog control signal into a digital signal, and this digital signal is provided to a controller 68. The controller 68 determines a digital control signal for the PLL 62 and provides this to the PLL 62. As the skilled person will be aware, in a PLL system, if the phase of the VCO 64 differs from the phase of the reference oscillator 61, the digital control signal corrects the VCO phase.

Movements of air, fluid and/or tissue in the body effectively detune the characteristics of antenna 12 (because of the reflected inductance), and the digital control signal counters this detuning and corrects the phase of the VCO 64. The digital control signal therefore carries information regarding the movements of the air, fluid and/or tissue, and the controller 68 determines an output signal 70 from the digital control signal that represents or contains the information on the movements of air, fluid or tissue in the body of the subject. Although this output signal 70 does not carry the actual phase and amplitude information, the physiological characteristics (e.g. heart rate, breathing rate) are clearly observable.

The correction signal $V_{tune}$ that is required to keep the VCO 64 at the required frequency is used to measure amplitude and/or phase shifts due to movements of air, fluid and/or tissue in the body of the subject. The phase shifts tend to dominate the amplitude changes. The PLL correction signal (the digital control signal output by the controller 68 derived from the analog PLL correction signal) is used to determine the output signal 70. For example the output signal 70 can correspond to the digital control signal with suitable filtering and/or down-sampling to improve the signal-to-noise ratio.

The output signal hence carries a signal representative of the received electromagnetic signals, derived based on changes in the natural resonance frequency of the resonator 11 which are reflected in the correction signal.

In accordance with a further set of embodiments, an alternative signal processing means is implemented in which sensed signals from the antenna 12 are first processed to reduce their frequency by mixing them with a further reference oscillatory signal of a different frequency and applying a filter which passes the differential frequency. This allows the subsequent signal processing to be performed in a much lower frequency range, which reduces energy consumption and required processing power.

In particular, to reduce energy consumption and required computing power of the system, the signal processing is preferably performed in the digital domain. Digital dividers and counters draw current proportional with the operating frequency. Hence, to further save power it helps to lower the frequencies in the digital system by using a second reference oscillator frequency close to the frequency at which the antenna 12 is driven for generating the electromagnetic excitation signals, and at which the signals returning from the body are also oscillating. By mixing the returned high-frequency electromagnetic signals (typically at around 400-500 MHz) with another signal having a frequency different but close to that frequency (for instance at +/−50 MHz of the EM measurement frequency), and applying a low pass filter which passes the differential frequency (i.e., $f_{measurement}-$ $f_{reference}$), the signal processing (e.g., digital counter) can be performed in a much lower frequency range, which reduces the energy consumption and required processing power.

Figure 8:
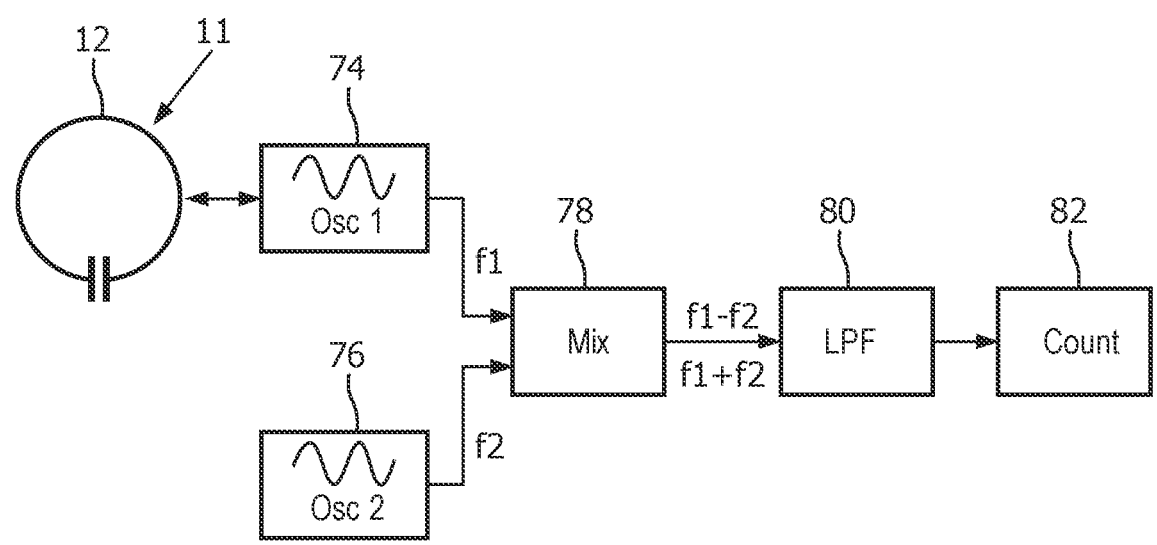
FIG. 8 shows a further example sensing system processing circuit in accordance with an embodiment.

One example of this processing scheme is illustrated in FIG. 8 which shows associated processing circuitry.

The system comprises a resonator having an antenna 12, the resonator coupled to a first oscillator ('Osc 1') 74 which generates an excitation signal for driving the resonator 11 to generate electromagnetic excitation signals for propagation into a body of interest (e.g. a body of a subject). Electromagnetic signals emitted back from the body in response are received at the antenna by inductive coupling 12 and the resultant signal is output from the resonator having frequency f1. A second (reference) oscillator ('Osc 2') 76 generates an oscillatory signal of a second frequency f2 being close to that of f1, for instance between f2=0.8*f1 and f2=1.2*f1 (i.e. within +/−10%-20% of f1).

A mixer ('Mix') 78 mixes the two frequencies f1 and f2, and a low-pass filter ('LPF') 80 then passes the differential frequency (i.e. f1–f2).

The resulting differential frequency signal is then passed to further processing components for deriving properties of the signal received from the body, e.g. in the example of FIG. 8, a counter 82.

In the example of FIG. 8, the first oscillator 74 performs the function of the signal generation means 14 of the system 10 (see FIG. 6) and the remaining shown components perform the function of the signal processing means 54 of the system.

In all examples of this processing approach, the result is that the RF measurement frequency of typically >200 MHz is reduced to a frequency of ~50 MHz, i.e. the difference between the two mixed frequencies f1, f2. Signals of such a frequency can be easily handled by microcontrollers and microprocessors. Such signals may for instance be directly handled by a microcontroller counter input.

In this way, the use of relatively higher energy-consuming elements such as RF phase-locked loop (PLL) systems and digital frequency dividers is avoided. The system accordingly requires significantly less current.

Alternatively, the use of the mixer and filter arrangement with a lower-frequency phase-locked loop (PLL) could be implemented to improve the quality of the system, although at the expense of greater power consumption.

Figure 10:
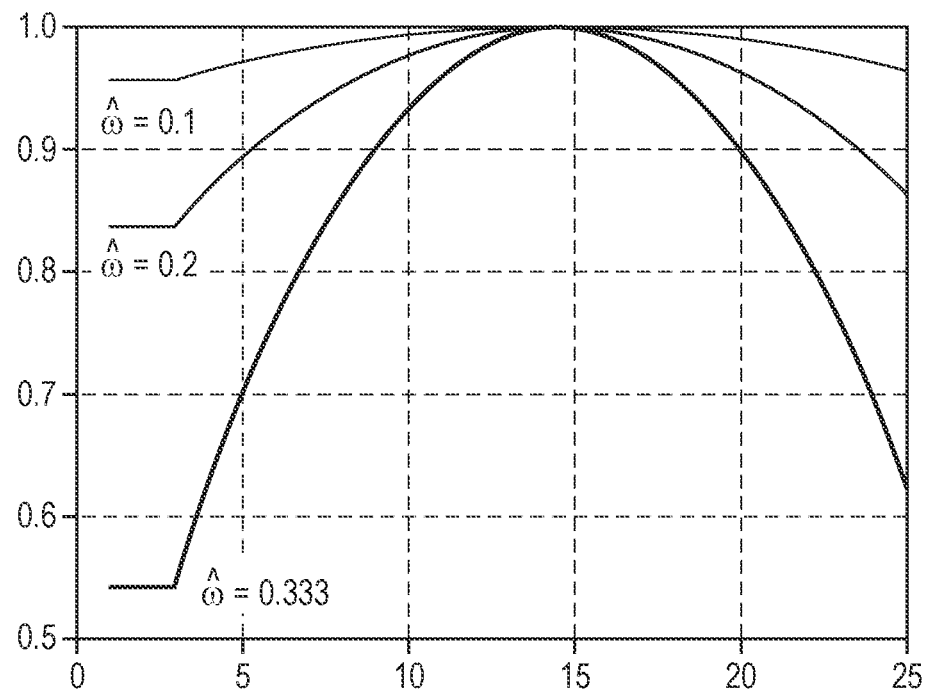
FIG. 10 shows variation in current phase around a measurement loop of an example sensing system for different normalized radial frequencies of electromagnetic signals.

A further advantage of the present set of embodiments is that mixing does not result in a loss of resolution. By contrast, use of a digital divider does result in such a loss. The sensed signal modulations at the down-mixed 28 MHz signal (taking the example of FIG. 10 presented above) are of the same amplitude (at same relative gain) as the modulations at the higher (e.g. 405 MHz) frequency.

The physiologically modulated 28-MHz signal is then output to low current processing elements, e.g. a counter-input of a frequency-counter of a microcontroller.

Microcontrollers are widely available having counter-inputs able to count frequency shifts in the range which typically occur in the body.

The use of frequency mixing and filtering, in combination with a digital counter, enables measurement of for instance physiological parameters such as vital signs including heartbeat and breathing with a low cost system. The antennas, oscillators, and mixer may in examples all be embedded in a PCB. Flexible circuit technology (such as flex-rigid technology) may also be used to further reduce the size and cost of components and of the overall system.

A test system has been built (which could be further optimized) which draws a 1 mA current per antenna, which is at least 10 times less current than similarly-performing digital systems.

All frequencies presented above are merely exemplary.

Other signal processing means may also be used. The skilled person will be aware of many standard approaches to measuring signals received at antennas, and any suitable approach may be used. A counter may for instance be used on its own to measure signals in further embodiments.

In the example of FIG. 1 presented above, a range of the normalized frequency $$\hat{\omega} \equiv \frac{\omega}{\omega_{ref}}$$

of the generated electromagnetic excitation signals of between 0.025 and 0.50 is used. This achieves advantageous performance over the prior art systems as explained above for reasons of improved signal to noise ratio and optimized sensitivity to magnetic rather electric signal components.

In particular, research has found that at values of $\hat{\omega}$ below 0.025, the signal to noise ratio of the sensed electromagnetic signal is significantly reduced, leading to higher motion sensitivity. More particularly, below this level, the signal strength is much decreased, and in most practical applications saturated by noise emanating from electronic noise, electromagnetic interference and noise from capacitive coupling with the surface of the body (i.e., direct coupling via electric fields and electrically induced charges).

Furthermore, below this normalized frequency, the oscillator has difficulty oscillating when N=1 (only a single turn loop), because of Ohmic losses that significantly reduce the Q-factor of the resonator at low normalized frequencies using N=1.

However, as discussed above, providing a resonator with N>1 (more than one loop), in order to enhance the Q-factor, is undesirable because it adds costs and complexity to the sensor, and also results in parasitic capacitances between the turns, thereby inducing non-uniform currents in the loop and inducing charges, even at low frequencies. This in turn makes the sensor more susceptible to noise artefacts originating from capacitive coupling between these induced charges in the loop and reciprocally induced surface charges on the body (induced by electric fields emitted by the loop charges).

In accordance with a more particular set of embodiments, the magnetic inductive sensing system may be configured such that a normalized radial frequency $$\hat{\omega} \equiv \frac{\omega}{\omega_{ref}}$$

of the electromagnetic excitation signals is from 0.025 to 0.25.

Within this range, current amplitude when sensing the signals received back from the body is substantially constant over the antenna loop. Above $\hat{\omega}$=0.25, the current amplitude varies to a greater extent over the antenna loop. Phase of current is also relatively constant around the antenna loop. These factors are significant limiting factors in achieving high signal strength and high quality signal.

Figure 9:
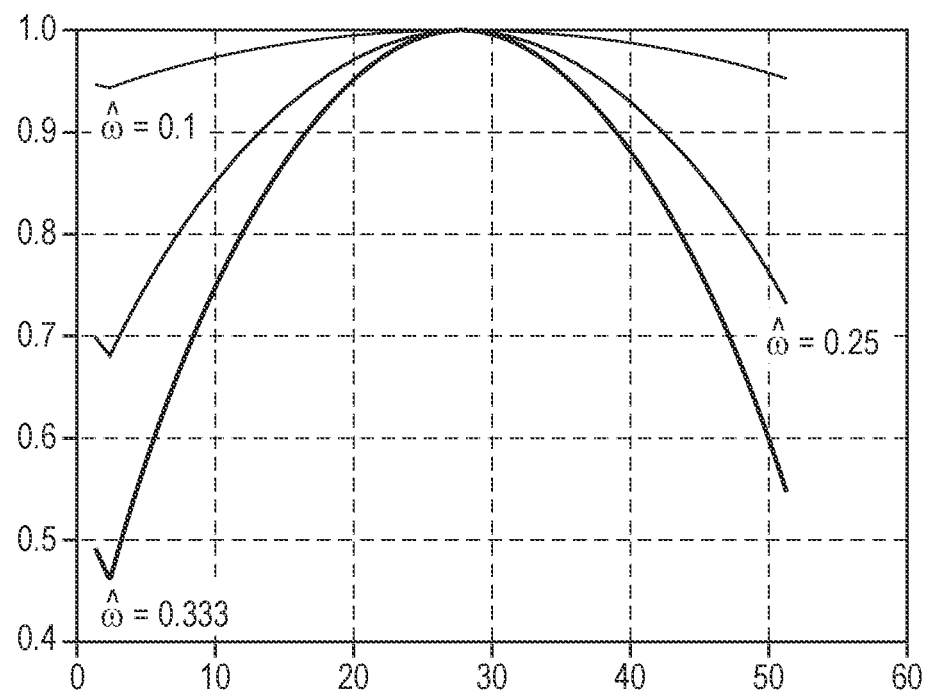
FIG. 9 shows variation in current amplitude around a measurement coil of an example sensing system for different normalized radial frequencies of electromagnetic signals.

This is illustrated in FIG. 9. FIG. 9 shows normalized current (y-axis) as a function of a segment index around the antenna loop (x-axis) for three different signals of different normalized radial frequencies $\hat{\omega}$. The corresponding $\hat{\omega}$ of each line is labelled in the graph.

It can be seen that above the normalized radial frequency $\hat{\omega}=0.25$, the homogeneity of the loop current rapidly becomes very poor. Inhomogeneous currents are highly disadvantageous because these result in accumulated charges which lead to capacitive coupling with the medium being examined. Capacitive coupling to the medium is a primary source of distortion (motion artefacts) for inductive sensors.

Hence by keeping below $\hat{\omega}=0.25$, uniformity of current and of current phase is significantly improved, but while maximizing signal strength, since it is known that higher $\hat{\omega}$ gives higher signal strength (explained above). This hence provides a good balance between signal strength (signal to noise ratio) and current and current phase uniformity.

In accordance with a further set of embodiments, the normalized radial frequency $\hat{\omega}$ of the excitation signals may be from 0.025 to 0.20. Below an upper limit of 0.20 for $\hat{\omega}$, radiation resistance is sufficiently low (<0.5Ω), current phase is relatively constant over the antenna loop and uniformity of current amplitude is further improved (<20% difference in current amplitude between any two points around the loop).

This is illustrated in FIG. 10. FIG. 10 shows that for $\hat{\omega}=0.20$, the current amplitude (y-axis) around the antenna circumference (x-axis) is relatively uniform, and of significantly greater uniformity than for $\hat{\omega}=0.333$ for instance.

Figure 11:
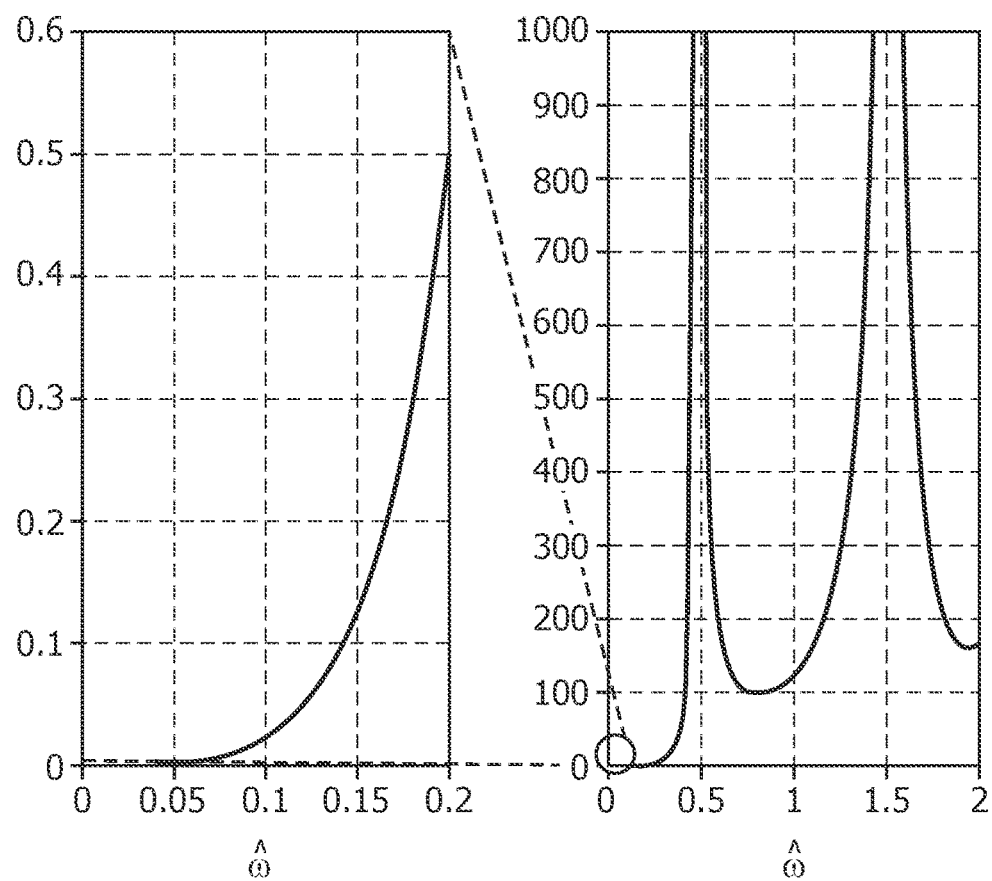
FIG. 11 shows the dependency of the impedance of an unshielded loop upon normalized radial frequency.

In addition to the above benefits, an upper level of 0.20 for $\hat{\omega}$ ensures that radiation resistance is kept within an optimally low range. This is illustrated in FIG. 11 which shows radiation resistance (y-axis; Ohms) as a function of $\hat{\omega}$ (x-axis). It can be seen that below a level of $\hat{\omega}=0.2$, radiation resistance is kept very low (below 0.5 Ohms). Hence 0.2 represents an optimal compromise between maximizing signal strength (signal to noise ratio) by maximizing $\hat{\omega}$ as much as possible, while maintaining a manageable level of radiation resistance.

This range is also particularly advantageous since above $\hat{\omega}=0.20$, some electrical effects begin to occur, resulting in the coil becoming sensitive to the electric field component of the EM signals received back from the body (which interferes with the sensitivity to magnetic field signals). Below $\hat{\omega}=0.20$, it has been found that the sensing system remains strongly magnetically sensitive, without building up significant electrical charges along the single antenna loop wire.

In accordance with a further set of embodiments the system 10 may be configured such that the normalized radial frequency $\hat{\omega}$ of the excitation signals is from 0.04 to 0.25. A lower limit of 0.04 is preferred since it results in higher signal strength (than 0.025 for instance) while still maintaining the benefits of very low radiation resistance (~0.01Ω), constant current phase over the antenna loop and constant current amplitude over the antenna loop.

It has been found that a normalized radial frequency $\hat{\omega}$ above 0.04 provides a signal of strength sufficiently high that the signal is reliably robust against noise across a wide range of practical applications. In certain scenarios (although not all), electromagnetic signals below this normalized frequency can become distorted by noise artefacts originating from capacitive coupling with the tissue surface (i.e., electric coupling with the surface of the body due to electrically induced charges). For conveniently-sized sensors of e.g. radius=1 to 3 cm, it has been found that signal strength is doubled compared to signals using normalized radial frequency of around 0.025. Breathing signals (signals indicating breathing function) have in particular been found to have significantly higher signal strengths.

In accordance with a further set of embodiments the system 10 may be configured such that electromagnetic excitation signals have a frequency of from 30 MHz to 1000 MHz.

The frequency here refers to absolute frequency, rather than radial frequency.

In accordance with these embodiments, an absolute frequency requirement is provided. Accordingly, since $$\hat{\omega} \equiv \frac{\omega}{\omega_{ref}}$$

and $\omega=2\pi f$, a corresponding requirement is imposed upon $\omega_{ref}=2\pi c/l$, meaning that the circumferential length l of the antenna loop must be configured accordingly.

This frequency range is beneficial because signal strength becomes significantly larger above f=30 MHz. This is particularly so for relatively smaller sized loops (radii in the range of 1-3 cm). In this case, where for instance the signal is measured by changes in resonance frequency of the resonator (as described above), the frequency shift signal (real part of reflected inductance) quickly becomes much stronger when going into this range, by both an increase in signal strength, and also a movement in the phase of the reflected inductance towards the real part.

This frequency range is also particularly advantageous when using a signal processing means in the form of a mixer-counter. The absolute changes in the resonator resonance frequency due to, for instance, breathing when using f<30 MHz can be below 1 kHz. When using a slope counter, the quantization noise of the number of counts in the signal is readily visible at this operating frequency.

When increasing the absolute frequency above f>30 MHz the influence of quantization noise on the signal will in most cases cease to be problematic. This is described in greater detail below.

In addition, it is beneficial to maintain frequency below 1000 MHz in order to optimize penetration depth. At frequencies above 1000 MHz, penetration depth of electromagnetic signals start to become prohibitively small for measuring physiological parameters, e.g. lung or heart signals.

In accordance with a further set of embodiments the system 10 may be configured such that electromagnetic excitation signals have a frequency of from 100 MHz to 1000 MHz.

At frequencies above 100 Hz, penetration depth is still sufficiently deep while signals become much stronger. Cardiopulmonary signals in particular have been found to become much stronger. In addition, the phase of the reflected inductance moves further toward the real part. This is beneficial where the signal generation means is adapted to measure changes in the resonator resonance frequency, which requires sensing the real part of reflected inductance.

In addition, above a frequency of 100 MHz, the quantization noise of e.g. a slope-counter signal processing means (at e.g. integration times of around 0.05 seconds) is almost negligible relative to the signal strength.

In accordance with a further set of embodiments the system 10 may be configured such that electromagnetic excitation signals have a frequency of from 30 MHz to 500 MHz.

This absolute frequency range optimizes penetration depth, in particular for muscle. The signal strength at 500

MHz remains very high, while penetration depth is maintained relatively large (~5 cm for muscle—and more for other media).

This frequency range may also be preferred where power consumption is a concern, e.g. battery powered sensors. Below 500 MHz, the frequency is low enough that it does not significantly contribute to signal processing power consumption.

In accordance with a further set of embodiments the system 10 may be configured such that electromagnetic excitation signals have a frequency of from 100 MHz to 500 MHz.

This combines the benefits 100 MHz lower boundary and 500 MHz upper boundary discussed above.

Applying excitation signals to a body at such high frequencies is not known in the prior art. This is because it is commonly understood in the art that frequencies above around 30 MHz lead to a significant reduction in achievable penetration depth, whilst increasing the required operating power.

The penetration depth or skin depth is defined as the distance over which the amplitude of an electromagnetic wave is decreased by a factor 1/e. More particularly, the skin depth or penetration depth $\delta$ is commonly defined as:

$$\delta \equiv \frac{1}{-\text{im}(k)} = \frac{1}{-\text{im}\left(\sqrt{\omega^2 \mu \left(\varepsilon - \frac{i\sigma}{\omega}\right)}\right)}$$

where k is wavenumber of the electromagnetic signals within the penetrated medium, $\omega$ is radial frequency of the signals, $\mu$ is permeability of the medium, $\varepsilon$ is permittivity of the medium and $\sigma$ is the conductivity of the medium.

The assumed loss in penetration depth at high frequencies derives from the so-called skin effect. This effect is seen for instance when an AC current flows in the vicinity of the surface of a conductor; the current density is seemingly pulled towards the surface of the medium, inhibiting current flow beneath the surface. The higher the frequency of the electromagnetic signal, the stronger the effect. This effect is also what happens in biological tissues penetrated by an inductive sensor: at higher frequencies, the induced eddy currents are effectively "pulled" towards the surface of the body, thereby cancelling the incoming magnetic field deeper in the tissue. The skin effect thus has a reducing effect on the penetration depth of an inductive sensor.

However, inventors of the present invention have found that in fact the reduction in penetration depth, while real, is much less significant than previously thought. In particular, it has been found that the reduction in achievable penetration depth does not become prohibitive to effective inductive sensing until frequencies of in excess of around 1000 MHz are reached. This is particularly the case in applications pertaining to investigating breathing function. These embodiments hence allow greater penetration depth than is currently known in the art.

Figure 12:
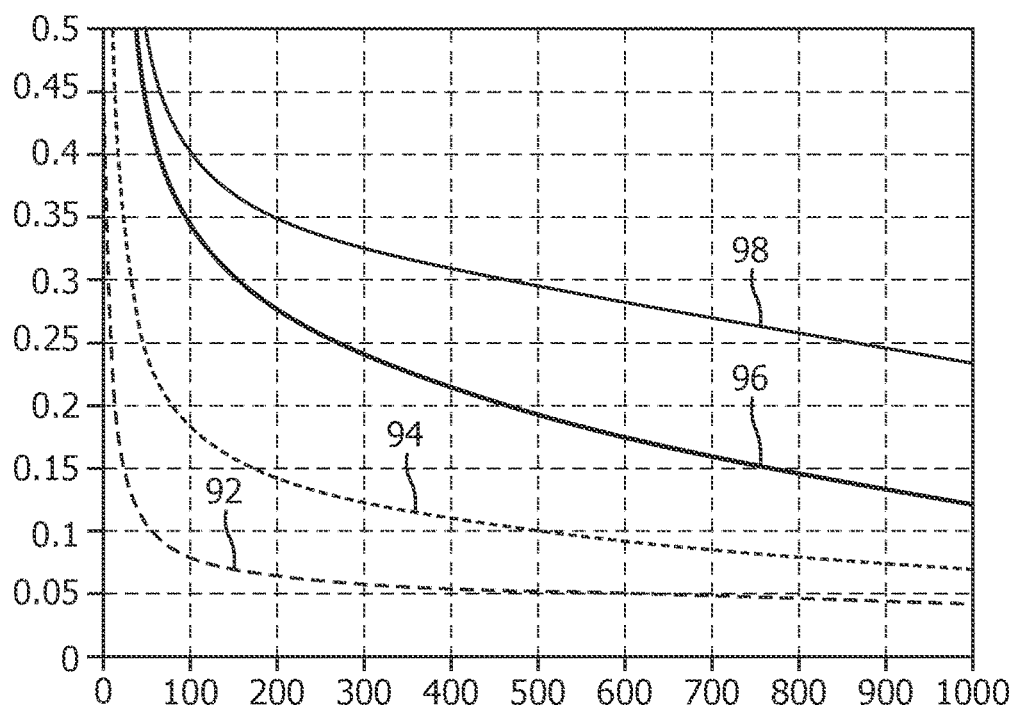
FIG. 12 penetration depth of excitation signals as a function of frequency of the signals for signals propagated through different media.

This is illustrated in FIG. 12 which shows penetration depth of generated excitation signals (y axis; meters) as a function of frequency of the signals (x axis; MHz) for signals propagated through four different media. Line 92 represents signals propagated through muscle, line 94 signals propagated through bone cancellous, line 96 signals propagated through bone cortical, and line 98 signals propagated through fat.

The graph shows that the loss of penetration depth with increasing frequency varies for different media. Waves penetrate very well through fat (line 98) even at very high frequencies, and relatively well through bone (lines 94 and 96). The waves penetrate less well through muscle, but even at frequencies at and above the previously assumed upper limit of 30 MHz, it can be seen that penetration depth is still in excess of 10 cm. It can be seen therefore that for a typical body comprising multiple layers of skin, fat, muscle and bone, penetration depth will be more than adequate to reach internal organs such as lungs or heart even at the frequencies used in this invention.

As noted above, the inductive sensor is based on coupling with magnetic components of reflected electromagnetic signals. Electrical (e.g. capacitive) coupling is undesirable as it masks the desired magnetic fields and saturates the detected signal. Signal to noise ratio is consequently reduced.

In accordance with one or more advantageous embodiments therefore, the sensing system may further comprise shielding means for shielding the antenna from electrical components of the reflected electromagnetic signals and/or for blocking electrical components of outgoing excitation signals.

A benefit of the shielding is that it allows the loop antenna to be operated at higher frequencies while ensuring the sensor is not rendered more sensitive to capacitive coupling with the body being probed. As noted above, accumulated electrical charge in the loop can in some circumstances capacitively couple to the patient thereby inducing electrical surface charge in the patient. This effect is detrimental because it masks the desired magnetic signal that originates from inside the body.

By adding electromagnetic shielding, potentially detrimental electric fields generated by the loop current will be contained around the loop, preventing coupling with the body being probed.

In one set of embodiments therefore, the system may further comprise a blocking shield arranged to intercept electromagnetic signals propagating to or from the antenna, the shield comprising an electrically conductive body for blocking electrical components of incident signals, and wherein the body delimits at least one non-conductive gap for inhibiting induction of eddy currents within the body.

When electromagnetic fields propagate to or from the antenna, the magnetic field components falling incident at any conductive body (including a shield) induce through magnetic induction (Faraday's law of induction) eddy currents within the body. In a shield, it is this which provides the magnetic field shielding effect since the eddy currents in turn induce a magnetic field of reverse directionality to that which was originally incident (Lenz' Law), thereby opposing or cancelling the original propagated magnetic field oscillations. Thus the magnetic field components are effectively blocked.

By including in the shield con-conductive gaps, the eddy currents cannot form, and hence the opposing field components which cancel out the propagating magnetic field oscillations are not generated. The magnetic field components of electromagnetic signals can hence travel through the shield.

By contrast, shielding of the electric field components, which operates via a different physical principle, continues to occur. Electric field shielding occurs through redistribution of electric charges within the shield's body upon incidence of electric field components of electromagnetic signals. Incidence of fields on one side of the shield redistributes the charges in such a way that that they cancel the field components' effects on the alternate side.

Thus the shielding approach of the present invention efficiently blocks propagation of electric field components while permitting passage of magnetic field components. The parasitic effects of the electric fields are therefore suppressed, and signal to noise ratio of a resulting measurement signal derived from signals received at the antenna is increased.

In one advantageous set of embodiments, a loop of the antenna may be broken by an opening, the opening being bridged by a capacitor to thereby form a resonator, and wherein the system comprises a signal processing means, the means being electrically coupled to the resonator via only a single point of the antenna, located on one side of the opening.

The consequence of this is that the resonator is only loosely coupled to the signal processing means, with the beneficial effect that the signal processing means does not heavily load the antenna loop. This improves the sensitivity of the signal-processing means system to incident electromagnetic signals.

The system has a large number of potential applications.

One particularly advantageous area of application is that of probing the human or animal body. The system allows for measurement or other analysis of movement of air of fluid (e.g. blood) within the body or of the expansion or contraction of organs or vessels such as the heart, the lungs or blood vessels for example.

The present application is directed in particular to a physiological sensing system. The system may comprise a processor for processing signals received by the antenna to derive one or more physiological parameters.

Embodiments of the invention allow for much greater signal strength than known systems by reason of the provided optimizations for normalized radial frequency of electromagnetic signal strength. Hence a powerful system is provided for probing the human and animal body non-invasively.

Any embodiment of the invention may be advantageously applied to measuring vital signs in accordance with one set of examples. This includes for instance heart rate, pulse rate, breathing capacity and breathing rate.

Although the present application is directed in particular to a physiological parameter inductive sensing system, the inventive concept is not limited in its application only to the sensing of physiological parameters. In general, embodiments of the system described in this disclosure may be used to probe internal properties of any body or object in which there is capacity for eddy currents to form in response to application of oscillating magnetic fields.

The system may be useful for instance for probing systems with dynamic interiors, i.e. interiors in which composing parts or portions move or change in size, since such changes and movements cause detectable modulations in sensed signals, allowing for measurement and other analysis.

As well as detecting dynamic changes in local volumes of regions of a body, the system is also highly useful for measuring conductive and dielectric properties of bodies.

The system could in examples for instance be used for measuring conductivity of a fluid through a container wall without direct galvanic contact, or the ripeness of fruit without the need for galvanic contact with the inside of the fruit.

In the detailed description above, the normalized radial frequency is defined as $$\hat{\omega} \equiv \frac{\omega}{\omega_{ref}},$$

where $\omega_{ref}=2\pi c/l$ and c=the speed of light.

This speed of light value may be interpreted more generally as the phase velocity of light in the medium surrounding the loop when it is used. Thus, the speed of light referred to is typically the speed of light in air (since typically the antenna is used in air) but it may more generally be considered to be the phase velocity of light in the medium surrounding the antenna. Thus, the invention may equally be applied when the antenna is not surrounded by air but by another medium.

Thus, the equation $\omega_{ref}=2\pi c/l$ becomes $\omega_{ref}=2\pi Vp/l$ where Vp is the phase velocity of light in the medium surrounding the loop when it is used.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A physiological parameter inductive sensing system for sensing electromagnetic signals emitted from a body in response to electromagnetic excitation signals propagated into said body, the system comprising:
    a loop resonator for inductively coupling with said electromagnetic signals emitted from the body, the resonator comprising a loop antenna and an electrically coupled capacitor, the loop of the antenna having only a single turn of circumferential length l, and
    a signal generation circuit adapted to excite the resonator to generate the electromagnetic excitation signals having a radial frequency ω for propagating into said body, wherein a normalized radial frequency $$\hat{\omega} \equiv \frac{\omega}{\omega_{ref}}$$

of the electromagnetic excitation signals is from 0.025 to 0.50, where $\omega_{ref}=2\pi c/l$ and c=the speed of light; and
    a signal processing circuit configured to sense said electromagnetic signals emitted from the body based on detecting electrical changes in the loop antenna indicative of changes in a measurable inductance of the loop while the loop is generating said excitation signals.

2. The physiological parameter inductive sensing system as claimed in claim 1, wherein the normalized radial frequency $\hat{\omega}$ of the electromagnetic excitation signals is from 0.025 to 0.25.

3. The physiological parameter inductive sensing system as claimed in claim 1, wherein the normalized radial frequency $\hat{\omega}$ of the electromagnetic excitation signals is from 0.04 to 0.25.

4. The physiological parameter inductive sensing system as claimed in claim 1, wherein the signal generation circuit is adapted to excite the resonator to resonate at a radial frequency ω in order to generate the excitation signals having radial frequency ω.

5. The physiological parameter inductive sensing system as claimed in claim 4, wherein the resonator is provided having a natural resonance frequency of ω in order to facilitate exciting of the resonator at a radial frequency of ω, and optionally wherein the capacitor is selected for tuning the natural resonance frequency of the resonator.

6. The physiological parameter inductive sensing system as claimed in claim 1, wherein the system comprises a signal processing circuit adapted to process signals received at the antenna and to downscale a frequency of the signals by mixing each signal with a reference oscillatory signal of a different frequency, and apply a differential filter to derive an output signal having a frequency being the difference between the frequency of the oscillatory signal and the received signal.

7. The physiological parameter inductive sensing system as claimed in claim 6, wherein the frequency of the reference oscillatory signal and the frequency of the received signals is from 10% to 20% apart.

8. The physiological parameter inductive sensing system as claimed in claim 1, wherein a frequency of the electromagnetic excitation signals is from 30 MHz to 1000 MHz.

9. The physiological parameter inductive sensing system as claimed in claim 1, wherein a frequency of the electromagnetic excitation signals is from 100 MHz to 1000 MHz.

10. The physiological parameter inductive sensing system as claimed in claim 1, wherein a frequency of the electromagnetic excitation signals is from 30 MHz to 500 MHz.

11. The physiological parameter inductive sensing system as claimed in claim 1, wherein a frequency of the electromagnetic excitation signals is from 100 MHz to 500 MHz.

12. The physiological parameter inductive sensing system as claimed in claim 1, wherein the loop of the antenna has a radius of between 15 mm and 20 mm; or the loop of the antenna has a radius of between 90 and 110 mm.

13. The physiological parameter inductive sensing system as claimed in claim 1, wherein the system comprises a signal processing circuit adapted to process signals sensed by the antenna to derive one or more physiological parameters.

14. A physiological parameter inductive sensing method comprising sensing electromagnetic signals emitted from a body in response to electromagnetic excitation signals propagated into said body, the method comprising:
  exciting a loop resonator to generate the electromagnetic excitation signals having a radial frequency ω and directing the signals into said body, wherein the resonator comprises a loop antenna and an electrically coupled capacitor, the loop antenna having only a single-turn loop of circumferential length l;
  using the loop resonator to inductively couple with the electromagnetic signals emitted from the body in response to the excitation signals; and
  sensing said electromagnetic signals emitted from the body based on detecting electrical changes in the loop antenna indicative of changes in a measurable inductance of the loop while the loop is generating said excitation signals,
  wherein a normalized radial frequency $$\hat{\omega} \equiv \frac{\omega}{\omega_{ref}}$$

of the electromagnetic excitation signals is from 0.025 to 0.50, where $\omega_{ref}=2\pi c/l$ and c=the speed of light.

15. The method as claimed in claim 14, wherein the normalized radial frequency $\hat{\omega}$ of the electromagnetic excitation signals is from 0.025 to 0.25.

16. The method as claimed in claim 14, wherein the normalized radial frequency $\hat{\omega}$ of the electromagnetic excitation signals is from 0.04 to 0.25.

17. The method as claimed in claim 14, wherein the signal generation circuit is adapted to excite the resonator to resonate at a radial frequency ω in order to generate the excitation signals having radial frequency ω.

18. The method as claimed in claim 17, wherein the resonator is provided having a natural resonance frequency of ω in order to facilitate exciting of the resonator at a radial frequency of ω.

19. The method as claimed in claim 14, further comprising:
  processing signals received at the antenna and to downscale a frequency of the signals by mixing each signal with a reference oscillatory signal of a different frequency; and
  applying a differential filter to derive an output signal having a frequency being the difference between the frequency of the oscillatory signal and the received signal.

20. The method as claimed in claim 19, wherein the frequency of the reference oscillatory signal and the frequency of the received signals is from 10% to 20% apart.

* * * * *